(12) United States Patent
Coulombe et al.

(10) Patent No.: US 7,608,839 B2
(45) Date of Patent: Oct. 27, 2009

(54) PLASMA SOURCE AND APPLICATIONS THEREOF

(75) Inventors: Sylvain Coulombe, Notre-Dame-de-L'ile-Perrot (CA); Sara Yonson, Ottawa (CA); Valerie Leveille, Montreal (CA); Richard Leask, Montreal (CA)

(73) Assignee: McGill University, Montreal (CA)

( * ) Notice: Subject to any disclaimer, the term of this patent is extended or adjusted under 35 U.S.C. 154(b) by 384 days.

(21) Appl. No.: 11/383,581

(22) Filed: May 16, 2006

(65) Prior Publication Data

US 2007/0029500 A1 Feb. 8, 2007

Related U.S. Application Data

(60) Provisional application No. 60/705,443, filed on Aug. 5, 2005.

(51) Int. Cl.
*H01J 27/00* (2006.01)

(52) U.S. Cl. .................. 250/426; 250/423 F; 606/41

(58) Field of Classification Search ................. 250/426
See application file for complete search history.

(56) References Cited

U.S. PATENT DOCUMENTS

| | | | | |
|---|---|---|---|---|
| 3,467,471 A * | 9/1969 | Berry et al. | ................ | 356/36 |
| 4,821,508 A * | 4/1989 | Burton et al. | ............... | 60/203.1 |
| 5,970,993 A * | 10/1999 | Witherspoon et al. | ........ | 134/1.1 |
| 6,126,779 A * | 10/2000 | Gillespie et al. | ............ | 156/348 |
| 6,475,215 B1 * | 11/2002 | Tanrisever | ................ | 606/45 |
| 6,503,816 B2 * | 1/2003 | Ito et al. | ................ | 438/485 |
| 6,723,091 B2 * | 4/2004 | Goble et al. | ................ | 606/41 |
| 6,958,063 B1 * | 10/2005 | Soll et al. | ................ | 606/41 |

OTHER PUBLICATIONS

Laroussi, M. et al.; New Journal of Physics (2003) vol. 5; 41.1-41.10.
Roth, J.R. et al.; IEEE Transactions on Plasma Science (2000) vol. 28; 56-63.
Bruil, A. et al.; Journal of Colloid and Interface Science (1994) 165; 72-81.
Stoffels, E. et al.;Journal of Physics D: Appl. Physics (2003) 36; 2908-2913.
Schmalenberg, K.E. et al.; Biomaterials (2004 ) 25; 1851-1857.
Ichiki, T. et al.; Journal of Applied Physics (2004); vol. 95, No. 1; 35-39.
Koinuma, H. et al.; Applied Physics Letters (1992) vol. 60, No. 7; 816-817.
Jeong, J. Y. et al.; Journal Vac. Science and Technology (1999) A 17(5); 2581-2585.

(Continued)

*Primary Examiner*—David A. Vanore
*Assistant Examiner*—Phillip A. Johnston
(74) *Attorney, Agent, or Firm*—Goudreau Gage Dubuc

(57) ABSTRACT

A low-power atmospheric pressure plasma source, comprising a plasma-forming region for injection of a plasma-forming gas; an excitation region for injection of a source of reactive species downstream of the plasma-forming region; and a narrow converging plasma exit for producing a narrow plasma jet, the source being electrically decoupled from a substrate under treatment by the plasma jet. The present source may find applications for example for skin treatment, etching of skin cancer cells, detachment of cells, removal of skin pigmentation and deposition of temporary organic films.

16 Claims, 12 Drawing Sheets

OTHER PUBLICATIONS

Park, J. et al.; Journal Applied Physics (2001) vol. 89, No. 1; 20-28.
Guerra-Mutis, M.H. et al.; Plasma Sources Sci. Technol. (2003) vol. 12; 165-169.
Kikuchi, T. et al.; J. Phys. D: Appl. Phys.(2004); 37; 1537-1543.
Yoshiki, H. et al.; Jpn. J. Appl. Phys. (2004) vol. 41; 5797-5798.
Jin, Q. et al.; Spectrochimica Acta (1991) vol. 46B; No. 3; 417-430.
Stonies, R. et al.; Plasma Sources Sci. Technol. (2004) 13; 604-611.
Bilgic, A.M. et al.; Spectrochimica Acta Part B 53 (1998) 773-777.
Storek, D. et al.; Z Gastroenterol (1993) vol. 31; 675-679 (in German).
Letard, J.C.; Acta Endoscopica (2000) vol. 30; Supplement 2; No. 3; 414-415.
Schreiber, J. et al.; Basic Science Investigations; Respiration (2000) vol. 67; 287-290.
Stoffels, E. et al.; Plasma Sources Sci. Technol. (2002) vol. 11; 383-388.
Kieft, I. E. et al.; New Journal of Physics (2004) vol. 6; 1-14.
Yokayama, T. et al.; J. Phys. D; Applied Physics (1990) vol. 23; 1125-1128.
Massines, F. et al.; Plasmas and Polymers (2001) vol. 6; Nos. 1/2; 35-49.
Moreau, S. et al.; Journal of Applied Physics (2000) vol. 88; No. 2; 1166-1174.
Moisan, M. et al.; International Journal of Pharmaceutics (2001) 226; 1-21.
Kelly-Wintenberg, K. et al.; Journal of Industial Mricrobiology & Biotechnology (1998) vol. 20; 69-74.
Sansonetti, J.E. et al; Handbook of Basic Atomic Spectroscopic Data; National Institute of Standards and Technology; Gaitherberg; 1-7, (2005).
Wang, S. et al.; Applied Physics Letters (2003) vol. 83; No. 16; 3272-3274.
Bell, E. et al.; Toxic In vitro (1991) vol. 5; No. 5/6, 591-596.
Bird, R.B. et al., Transport Phenomena, Department of Chemical Engineering (1960) John Wiley & Sons; 41 and 51-54.
Brown, S.C.; Basic Data of Plasma Physics (New York: AIP Press) (1993).
Baker, H. J.; Meas. Sci. Technol. (1996) 7; 1631-1635.
Demaw, D. et al.; The radio Amateur's Handbook (1979) 56th Edition; American Radio Relay League, Newington.
Malenfant, A. et al.; Pain; Research Papers (1998) 77; 241-251.
Ziegler, D. et al.; Pain; Clinical Section (1988) 34; 1-10.
Adams, R. D. et al.; Fifth Edition; Principles of Neurology (1993) (New York: McGraw Hill Inc.) 1394.
Gaydon, A. G.; The Spectroscopy of Flames (1957) Catalogue No. 594/4.
Lee, Y-H. et al.; Surface and Coating Technology (2001) 146-147; 474-479.
Seo, D-C. et al.; Journal of Physics D: Applied Physics (2001) vol. 34; 2854-2861.
Tanabe, K. et al.; Spectrochimica Acta (1983) vol. 38B; Nos. 1/2; 49-60.
Nersisyan, G. et al.; Plasma Sources Sci. Technol. (2004) vol. 13; 582-587.
Herzberg, G.; Atomic Spectra and Atomic Structure (New York: Dover publications) 1944.
Vacquié, S.; L'arc électrique; Science et Tehcniques de L'ingénieur (2000) (Paris: CNRS Éditions) (2000) pp. 237-253.
Yoshiki, H. et al.; Journal of Applied Physics (2001) vol. 40; L360-L362.
Kieft, I.E. et al.; IEEE Transactions on Plasma Science (2005) vol. 33; 771-775.
Fridman, G. et al.; Proc. 17th Int. Symp. on Plasma Chemistry (Toronto), Aug. 2005.
Coulombe, S. et al.; Pure Appl. Chem. (2005) vol. 78, No. 6; 1137-1146.
De, S. et al.; Abstract J. Biomater. Sci. Polym. Ed. (2005) vol. 16, No. 8; 973-989.
Van Kooten, T. G. et al.; Biomaterials (2004) vol. 25; 1735-1747.
Corning Incorporated 2005 Corning Cell Culture Selection Guide (New York: Corning).
BD Biosciences 2001 BD Falcon (TM) cell culture products (Bedford: Beckton, Dickson and Company).
Brown, I.G. et al.; Plasma Physics and Control. Fusion (2003) vol. 45; 547-554.
Ohl, A. et al.; Surface and Coating Technology (1999) 116-119; 820-830.
Miller, C. et al.; Biomaterials (2001) vol. 22; 1263-1269.
Schroder, K. et al.; Plasmas and Polymers (2002) vol. 7, No. 2; 103-125.
Kieft, I.E. et al.; Bioelectromagnetics (2004) vol. 25; 362-368.
Léveillé,V. et al.; Plasma Sources Sci. Technol. (2005) vol. 14; 467-476.
Umebayashi, Y. et al.; Journal of Biochemistry (2003) vol. 134; 219-224.
Djordjevi, V. B.; Abstract; International Review of Cytology (2004) vol. 237; 57-89.
Clément, F. et al.; European Phys. J. AP (2002) vol. 18; 135-151.
Tamada, Y. et al.; Polymer (1992) vol. 34; 2208-2212.
Léveillé, V. et al.; Astract: Proc. 17th int. Symp. on Plasma Chemistry; Department of Chemical Engineering, McGill University, Montreal, Canada; 2005.

* cited by examiner

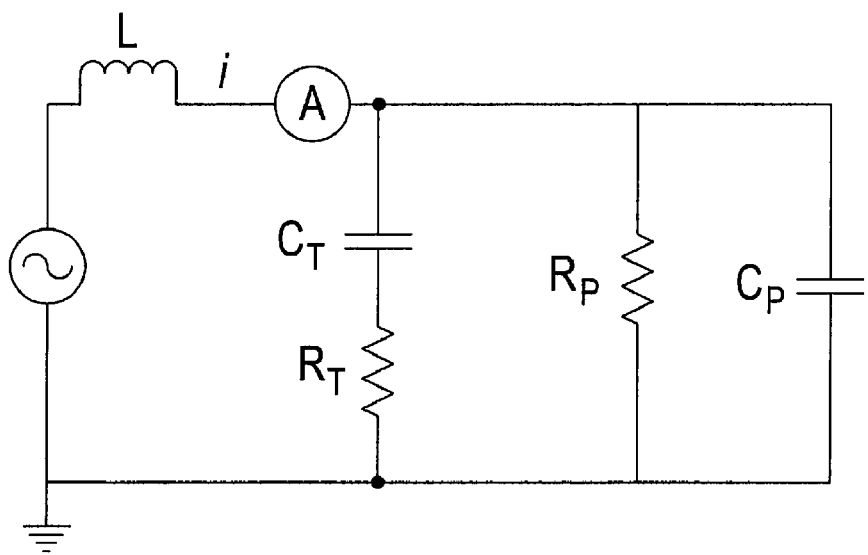
_FIG_7
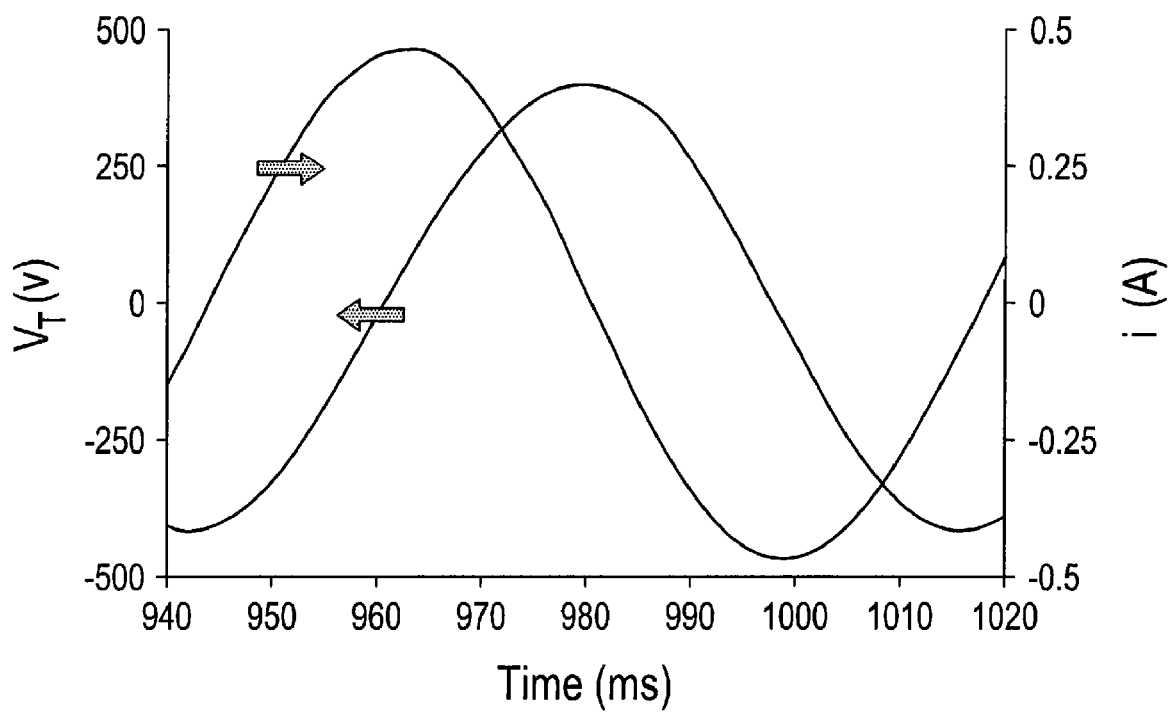
_FIG_8

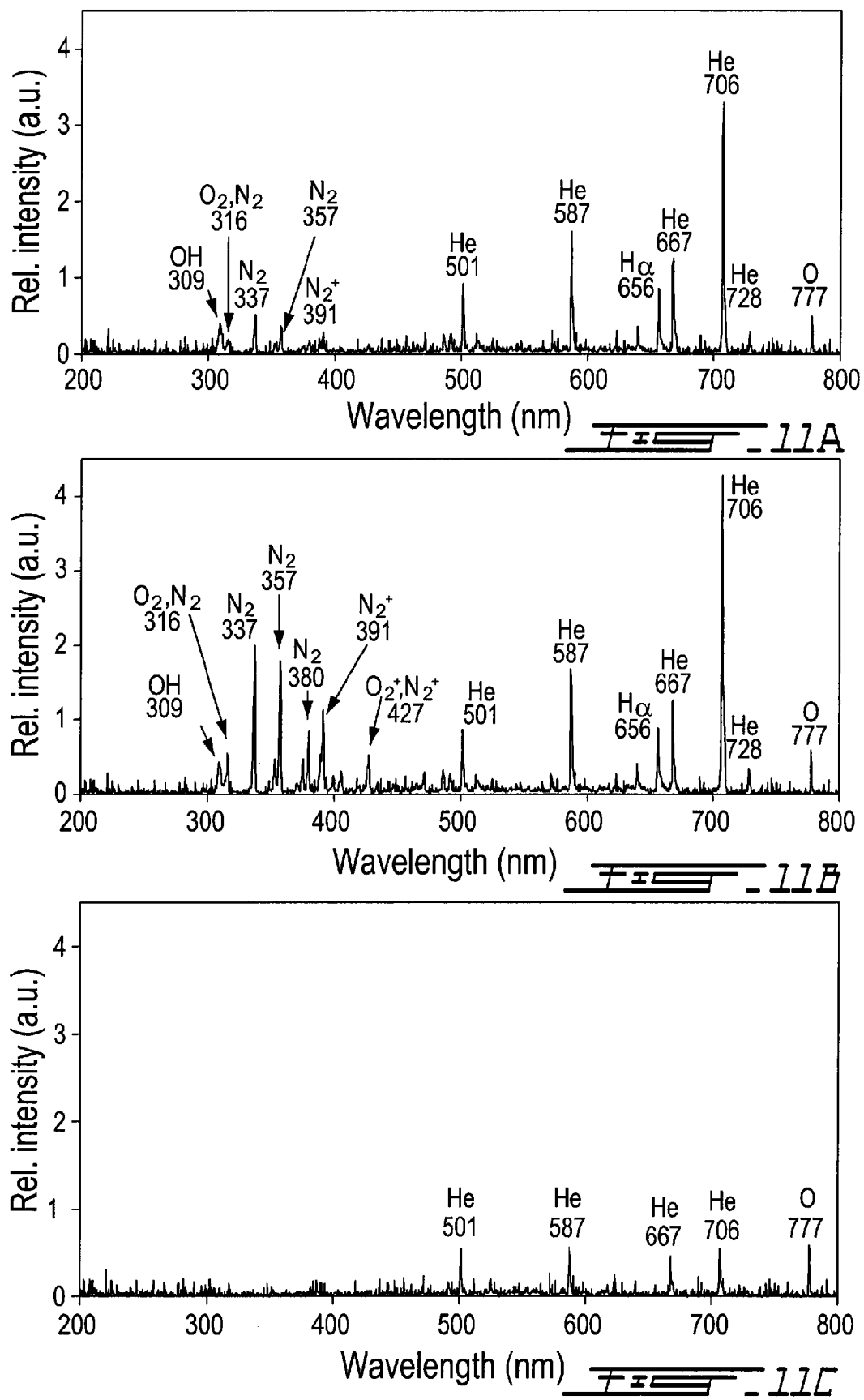

PLASMA SOURCE AND APPLICATIONS THEREOF

CROSS REFERENCE TO RELATED APPLICATIONS

This application claims priority on U.S. provisional application No. 60/705,443, filed on Aug. 5, 2005. All documents above and below are herein incorporated by reference.

FIELD OF THE INVENTION

The present invention relates to a plasma source and plasma treatment. More specifically, the present invention is concerned with a miniature atmospheric pressure plasma source and applications thereof.

BACKGROUND OF THE INVENTION

Plasmas, or ionized gases made up of excited atoms, ions, radicals and electrons, are widely used for modification of surfaces without affecting bulk properties of samples. Plasma treatments have been developed and used for more than 30 years in the microelectronics and textile industries, biomedical, environmental, materials and chemical process engineering fields, as well as in surgery. Plasmas offer a high-density source of energy and/or reactive species.

Atmospheric-pressure plasmas are used in a variety of materials processes. Traditional Atmospheric-pressure plasma sources include transferred arcs, plasma torches, corona discharges, and dielectric barrier discharges.

Plasmas are generally classified as thermal or non-thermal. Thermal plasmas are characterized by a high energy density and high gas and electron temperatures, which are nearly equal in value. Thermal plasmas are used where a high enthalpy source is required.

Non-thermal plasmas are characterized by a low energy density, and a significant difference between the temperature of the heavy species (the "gas") and the electrons. Non-thermal plasmas are chemically selective, more energy efficient and represent a lower thermal load to processed materials and surfaces. Non-thermal plasmas are well suited for the treatment of biological and biocompatible surfaces.

Non-thermal plasmas can be produced in controlled environments and under reduced pressure conditions. Non-thermal plasmas can also be produced under atmospheric pressure conditions in open-air configurations or controlled atmosphere conditions.

Non-thermal plasma sources come under various shapes for various applications, including large volume or large area plasma sources for bulk or large surface-area treatments, respectively, and plasma torches or jets for remote exposure applications.

The plasma-forming zone of the non-thermal plasma source, in the case of uniform plasma, is called the glow. The region of plasma extinction where the plasma species de-excite and recombine is called the afterglow.

The interest in atmospheric pressure non-thermal plasma sources for the modification and treatment of biological and biocompatible surfaces has grown considerably over the last decade. Such sources offer convenient means for sterilization (see for example: Laroussi M, Mendis D A and Rosenberg M 2003 *New J. Phys.* 5 41.1-41; Roth J R, Sherman D M, Ben Gadri R, Karakaya F, Chen Z, Montie T C, Kelly-Wintenberg K and Tsai P P-Y 2000 *IEEE Trans. Plasma Sci.* 28 56-63); surface functionalization (see for example: Bruil A, Brenneisen L M, Terlingen J G A, Beugeling T, Van Aken W G and Feijen J 1994 *J. Colloid Interface Sci.* 165 72-81), cell removal (see for example: Stoffels E, Kieft I E, Sladek R E J 2003 *J. Phys. D: Appl. Phys.* 36 2908-2913), microcontact printing of protein onto polymer substrates (see for example: Schmalenberg K E, Buettner H M and Uhrich K E 2004 *Biomaterials* 25 1851-1857) and tissue modification.

The development of such plasma sources is not without challenges. The main challenges include for example 1) the difficulty to sustain a stable and uniform glow discharge over large surface areas in film deposition and surface functionalization; 2) the need to maintain a high degree of non-thermal equilibrium to minimize the thermal load to the substrates of interest, while maintaining a high degree of chemical reactivity and 3) the extremely rapid recombination of the reactive species in the plasma afterglow when a torch configuration is used.

Several devices have been developed to produce relatively small non-thermal plasma streams at atmospheric pressure. A miniature inductively-coupled plasma (ICP) torch using an argon/halogen mixture was recently developed for localized and high rate etching of silicon wafers (see for example: Ichiki T, Taura R, Horiike Y 2004 *J. Appl. Phys.* 95 35-39). Miniature capacitively-coupled plasma torches using mixtures of He and halogen gases, or oxygen, have also been developed for local etching of silicon (see for example: Koinuma H, Ohkubo H, and Hashimoto T, 1992 *Appl. Phys. Lett.* 60 816-817) and etching of polyimide (see for example: Jeong J Y, Babayan S E, Schutze A, Tu V J 1999 *J. Vac. Sci. Technol. A: Vac. Surf. Films* 17 2581-2585). Other capacitively-coupled plasma torches have been developed for the treatment of heat sensitive materials (Park J, Henins I, Herrmann H W and Selwyn G S 2001 *J. Appl. Phys.* 89 20-28) and as a source of active species for the depletion of contaminants present in liquid hydrocarbons (Guerra-Mutis M H, Pelaez U C V and Cabanzo H R 2003 *Plasma Sources Sci. Technol.* 12 165-169). Single electrode configurations were also reported for silicon oxidation, synthesis of carbon nanostructures (Kikuchi T, Hasegawa Y and Shirai H 2004 *J. Phys. D: Appl. Phys.* 37 1537-1543) and removal of photoresist (Yoshiki H, Taniguchi K and Horiike Y 2002 *Jpn. J. Appl. Phys.* 44 5797-5798). There have been other miniature plasma sources developed for remote analytical systems, such as the microwave plasma torch (MPT), used as an excitation source for atomic spectroscopy (see for example: Jin Q, Zhu C, Borer M W, Hieftje G M 1991 *Spectrochim. Acta B* 46 417-430; Stonies R, Schermer S, Voges E and Broekaert J A C 2004 *Plasma Sources Sci. Technol.* 13 604-611; Bilgic A M, Prokisch C, Broekaert J A C, Voges E 1998 *Spectrochim. Acta B* 53 773-777).

These plasma sources share a number of common characteristics, including: 1) a high-frequency excitation (RF or microwave, except for Guerra-Mutis M H, Pelaez U C V and Cabanzo H R 2003 *Plasma Sources Sci. Technol.* 12 165-169), which favors the formation of a non-thermal plasma at atmospheric pressure under low-voltage excitation conditions (few hundred volts); 2) use of He or Ar as the main plasma-forming gas, 3) use of minute amounts of an additional gas as the source of reactive species, and 4) a configuration permitting the rapid transport of excited species to the surface of interest in remote exposure applications.

In the field of local bio-applications, atmospheric pressure plasma sources have been scarcely reported since the early 1990's. An argon plasma coagulation (APC) device, which uses a small rod as the powered electrode and the patient as the ground electrode, was commercialized as a small-scale electrocoagulation tool (Storek D, Grund K E, Gronbach G, Farin G, Becker H D 1993 *Z Gastroenterol.* 31 675-679 (in German)). It was demonstrated through clinical trials that the APC caused significantly less damage to tissues than YAG lasers. The APC produces an electrical discharge between the electrode and the lesion, which desiccates, coagulates, and devitalizes through heat effects (see Letard J C 2000 *Acta Endoscopica* 30 (S2) 414-415; Schreiber J, Hofman B, Schumann H J and Rosahl W 2000 *Respiration* 67 287-290).

Recently, the treatment of biological tissue and cells (Stoffels E, Kieft I E and Sladek R E J 2003 *J. Phys. D: Appl. Phys.* 36 2908; Kieft I E, Darios D, Roks A J M and Stoffels E 2005 *IEEE. Trans. Plasma Sci.* 33 771; Fridman G, Peddinghaus M, Fridman A, Balasubramanian M, Gutsol A and Freidman G 2005 *Proc. 17th Int. Symp. on Plasma Chemistry (Toronto)*), as well as the functionalization of surfaces to control cell adhesion, have been investigated (De S, Sharma R, Trigwell S, Laska B, Ali N, Mazumder M K and Mehta J L 2005 *J. Bio mater. Sci. Polym. Ed.* 16 973-989; van Kooten T G, Spijker H T and Busscher H J 2004 *Biomaterials* 25 1735-1747). Non-thermal, atmospheric pressure plasma sources are particularly suitable for use with heat-sensitive substrates. Having the bulk temperature of the plasma close to room temperature reduces the negative effects of thermal loads on such materials as human tissues and biodegradable polymers used in the construction of biomedical devices, while still being able to take advantage of the highly reactive nature of the plasma.

The treatment of biomaterials with non-thermal plasmas has been widely researched, and various technologies are used commercially in the modification of tissue culture vessels. Cell attachment is enhanced by modifying the culture dish surface using plasmas of various gas compositions to increase the amount of oxygen and/or nitrogen groups incorporated into the surface (Corning Incorporated 2005 *Corning cell culture selection guide* (New York: Corning); BD Biosciences 2001 *BD Falcon (TM) cell culture products* (Bedford: Beckton, Dickson and Company). The modifications enhance the hydrophilicity of the surface by the addition of polar groups, and increase cell adhesion. At the laboratory level, researchers have investigated plasma treatment to micropattern surfaces to study neuronal networks (Brown I G, Bjornstad K A, Blakely E A, Galvin J E, Monteiro O R and Sangyuenyongpipat S 2003 *Plasma Phys. Control. Fusion* 45 547-554), the fabrication of biosensors and the imitation of in-vivo cell patterning on implants to improve biocompatibility.

Currently, most plasma patterning is done using photolithographic techniques. A chemical coating is hardened with UV light through a laser-cut metal mask, and the unaffected areas are washed clean. The whole surface is plasma treated, functionalizing the areas not covered with the resist layer (Ohl A and Schrader K 1999 *Surf. Coat. Technol.* 116-119 820-830). The resist is removed, and the functionalized pattern is left on the surface. There are a few aspects of photolithography that inhibit its use on biomaterials. First, it has traditionally been used on glass or silicon surfaces, and the chemicals used in the process can accelerate the degradation of the polymers used as biomaterials (Miller C, Shanks H, Witt A, Rutkowski G and Mallapragada S 2001 *Biomaterials* 22 1263-1269) and introduce a source of contamination in cell culture. Secondly, masks are costly, and give only one pattern. Moreover, the masking process does not work well on curved surfaces. Schroder et al. (Schroder K, Meyer-Plath A, Keller D and Ohl A 2002 *Plasmas and Polymers* 7 103-125) have been successful in plasma micropatterning directly through a mask without using the chemical resist, however, they found that the mask was sensitive to handling and heat. The use of a miniature plasma source that is capable of 3-D movement could circumvent the present difficulties of micropatterning on unsymmetrical, biodegradable surfaces.

In addition to surface patterning, the possibility to perform tissue/cell treatment is of tremendous interest. A so-called plasma needle has been previously used to treat mammalian cells (Kieft I E, Broers J L V, Caubet-Hilloutou V, Slaaf D W, Ramaekers F C S and Stoffels E 2004 *Bioelectromagnetics* 25 362-368). At a power level of 0.1-0.3 W, Kieft et al showed cells could be detached and would reattach within four hours. The important role of media coverage was highlighted; too little and the cells dehydrated and died, and too much and the reactive species from the plasma did not reach the cell (Kieft I E, Darios D, Roks A J M and Stoffels E 2005 *IEEE. Trans. Plasma Sci.* 33 771). It was proposed that the adhesion molecules, both those responsible for cell-cell and cell-substrate binding, had been interrupted based on the visual inspection of the behaviour of the cells after treatment, and viability stains. Other potential oxidative effects on the cell due to plasma treatment include lipid peroxidation (the deterioration of the cell membrane due to the oxidation of the lipids), protein oxidation and cell death due to an imbalance of reactive oxygen and nitrogen species (ROS and RNS).

Technologies currently used to permeabilize cells include capillary microinjection, surfactants and electroporation, whose primary limitations are low throughput, cell death, and the need for cells in suspension, respectively. Inducing cell death restricts time dependent studies, while the trypsinization required to produce a cell suspension disrupts cell adhesion proteins, limiting the study of certain cell processes.

The present invention seeks to meet these needs and other needs.

SUMMARY OF THE INVENTION

More specifically, there is provided a low-power atmospheric pressure plasma source, comprising a plasma-forming region; an excitation region located downstream of the plasma-forming region; and a narrow converging plasma exit; wherein a plasma-forming gas is injected in the plasma-forming region at a flow rate of a few SLM and a source of reactive species is injected in the excitation region, the plasma-forming gas and source of reactive species producing a narrow plasma jet through the narrow converging plasma exit.

There is further provided a plasma-assisted treatment system, comprising a low-power atmospheric pressure plasma source, the source comprising a plasma-forming region; an excitation region located downstream of the plasma-forming region; and a narrow converging plasma exit; wherein a plasma-forming gas is injected in the plasma-forming region at a flow rate of a few SLM and a source of reactive species is injected in the excitation region, the plasma-forming gas and source of reactive species producing a narrow plasma jet through the narrow converging plasma exit.

There is further provided a method for cell modification using a low-power atmospheric pressure plasma source, the source comprising a plasma-forming region; an excitation region located downstream of the plasma-forming region; and a narrow converging plasma exit; wherein a plasma-forming gas is injected in the plasma-forming region at a flow rate of a few SLM and a source reactive species is injected in the excitation region, the source producing a narrow plasma jet through the narrow converging plasma exit.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 7 is a schematic of an electrical circuit used for impedance matching study of the system of FIG. 5;

FIG. 8 shows one cycle of the RF current (i) and voltage ($V_T$) signals applied to a present source operating with 1 SLM He;

FIG. 11 show emission spectra of the plasma jet ~1 mm downstream of the nozzle exit plane for $P_T$≈1 W: a) 1 SLM He, b) 1 SLM He with 10 SCCM $O_2$ in the capillary electrode, and c) 1 SLM He+1 v/v % $O_2$ as plasma-forming gas;

DESCRIPTION OF ILLUSTRATIVE EMBODIMENTS

Figure 1:
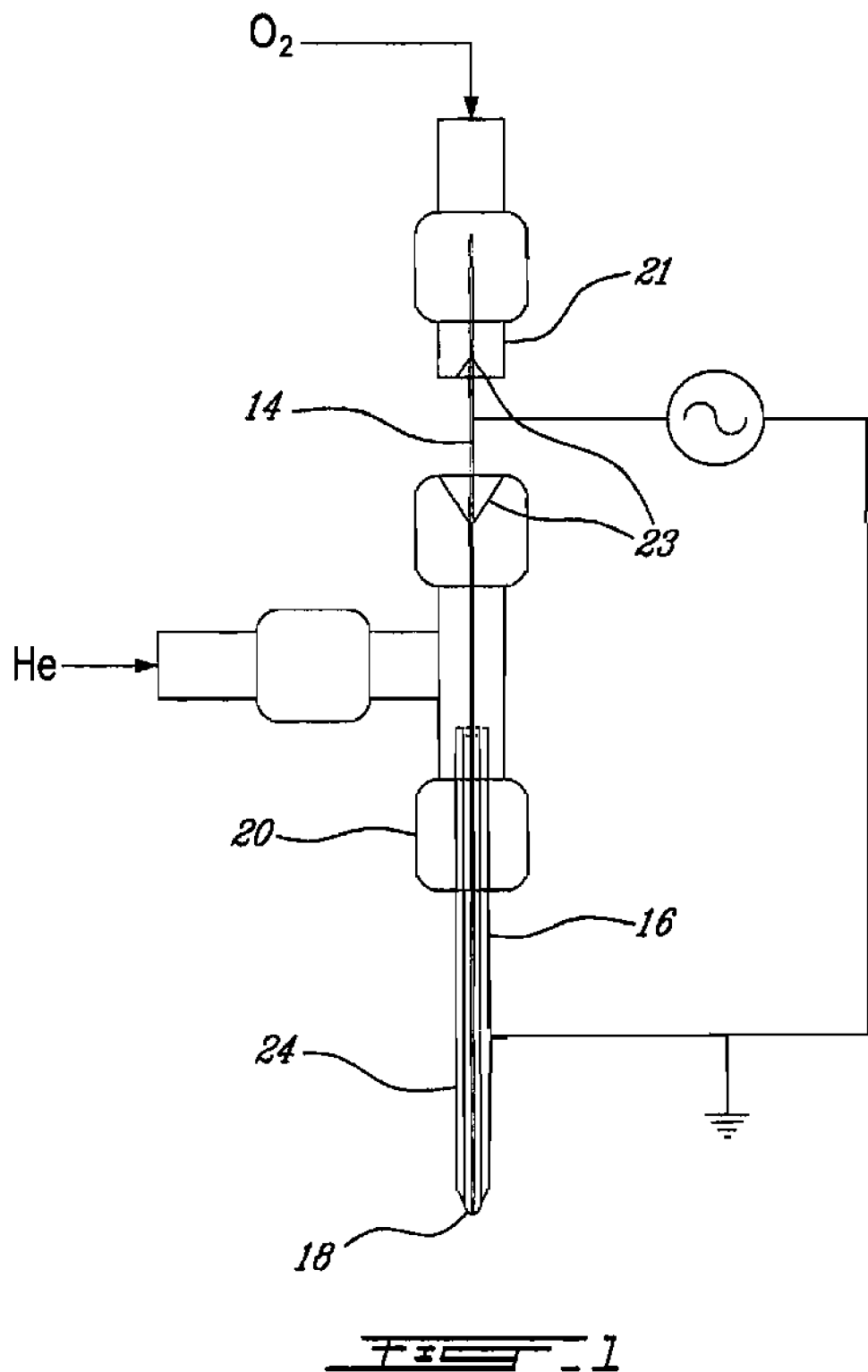
FIG. 1 is a schematic of a plasma source according to an embodiment of the present invention.

FIG. 1 of the appended drawings illustrates a plasma source according to an embodiment of a first aspect of the present invention.

The source comprises a powered electrode 14 and a ground electrode 24.

The powered electrode 14 is a stainless steel capillary tube for example, with typical inside and outside diameters of 0.0070±0.0005" (0.1778±0.0127 mm) and 0.0140±0.0005" (0.3556±0.0127 mm), respectively. The small outside diameter of the powered electrode 14 allows for the local enhancement of the electric field and thus, a considerable reduction of the breakdown voltage requirement.

The powered electrode 14 is centered in a quartz confinement tube 16 acting as a dielectric barrier. Typically, the confinement tube 16 has an internal diameter of 2 mm, and an exterior diameter of 4 mm, and the downstream end of the tube is shaped into a converging nozzle 18 of an ending diameter of 500 μm or less for example. An electrically conductive layer, such as silver paste for example, deposited on the external surface of the confinement tube 16, acts as the ground electrode 24.

A tip of the electrode 14 may be recessed by a few μm from the plane of the nozzle exit 18, so that the gap formed between the powered electrode 14 and an inner surface of the confinement tube 16 is very small, i.e. 822 μm-wide in a straight section of the confinement tube 16 and down to 72 μm for example at the nozzle exit 18 in case of perfect alignment in the middle of the nozzle exit.

The provision of such central electrode 14 allows for a number of features, including for example: a spatial decoupling of the plasma-forming region from the region of excitation and mixing of the source of reactive species (two distinct regions); a geometrical enhancement of the local electric field which effect leads to a confinement of the plasma zone (high plasma density) around the electrode 14 and to a reduction of the breakdown and sustaining voltages; a stable and low voltage operation of the plasma source independently of the nature of the source of reactive species; an injection of any gaseous, liquid or solid reactive materials and its gaseous carrier separately from the plasma-forming gas; an efficient mixing of the source of reactive species with the main plasma gas due to the high shear at the injection point; and a flexibility to position the point of injection of the source of reactive species anywhere inside the region of excitation.

Such a source is about 10 cm-long, and held together with a Teflon Swagelok® tee 20, and Teflon™ fittings 21 and 23 for example.

A plasma-forming gas (He for example) may be fed through the side arm of the tee 20, while reactive gases ($O_2$ for example) may be injected through the capillary electrode 14, or added to the plasma-forming gas for example. Alternatively, $O_2$ and He may be both injected axially and separately from the top of the torch, instead of from a side arm.

Under typical operating conditions in He, a glow discharge fills the entire annular space contained between the confinement tube 16 and the capillary electrode 14.

Injection of the source of reactive species inside the capillary electrode 14 downstream of the plasma-forming region allows the generation of a wide range of reactive species without affecting the properties and stability of the plasma.

The nozzle 18 at the end of the confinement tube 16 in combination with a relatively high flow rate of the plasma-forming gas (few SLM) allows an acceleration of the plasma flow and the formation of a narrow-diameter plasma jet. Furthermore, this arrangement favors the axial transport of the short-lived excited (reactive) species, generated by the plasma, to a remote surface to be treated. As people in the art will appreciate, such a feature allows treatments requiring a relatively abundant quantity of reactive species. Moreover, the important momentum transferred to the reactive species facilitates their penetration through the surface of interest, in case it is porous.

The very small plasma jet diameter (<500 μm) may be useful for example for precise surface treatment. Since a 500-μm plasma jet covers about 15 aligned mammalian cells (about 30 μm OD each), the present plasma source may be used for example for preventive cancer treatments, where the treatments must be localized on the region containing cancer cells, considering that currently available plasma torches have jet diameters much larger than 500 µm.

Figure 2:
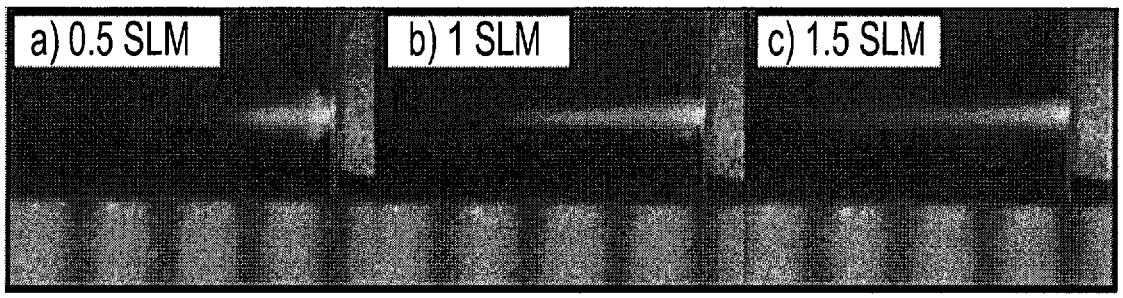
FIG. 2 show pictures of a plasma jet produced by the present torch operating at ≈1 W for different He flow rates.

In FIG. 2, pictures of the jet are presented for three different flow rates of helium and a torch power of about 1 W (no $O_2$ added). Under typical operating conditions, the plasma jet is approximately 2 to 4 mm long (the jet diameter at the nozzle is 500 µm). One can distinguish a bright (whitish) plasma core surrounded by a blue plume. The whitish plasma core is characteristic of the He plasma emission while the bluish afterglow is attributable to the optical emission from species produced from the $N_2$ and $O_2$ molecules present in the ambient air and entrained in the plasma afterglow. The pictures reveal that an increase of the He flow rate elongates the jet. Higher axial plasma flows are beneficial to the transport of excited reactive species to a remote substrate since the ratio of the recombination time scale over the convective transport time scale is higher. On the other hand, larger flow rates involve higher He consumption and more momentum transfer to the substrates, which, in the case of bio-applications, might not be mechanically strong (ex. cells attached on a Petri dish). The picture of the plasma jet in FIG. 3a best reveals a structure near the nozzle exit that might originate from sonic flow conditions.

Figure 3:
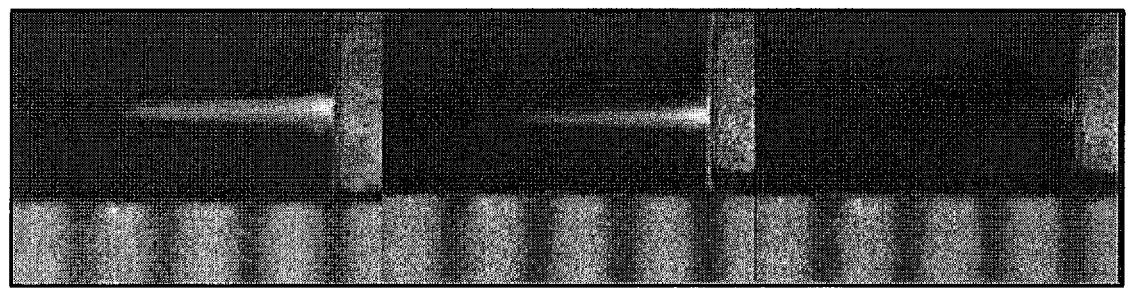
FIG. 3 show pictures of the plasma jet at ≈1 W and 1 SLM He (left) with 10 SCCM $O_2$ injected through the capillary electrode (center) or with 1 v/v % $O_2$ added to the plasma-forming gas (right)

FIG. 3 presents a comparison of the visual appearance of the plasma jet when $O_2$ is injected in the capillary electrode (10 SCCM $O_2$, FIG. 3b) or added to the plasma-forming gas (1 v/v % of $O_2$ in He is equivalent to 10 SCCM in the capillary electrode, FIG. 3c) with a helium flow of 1 SLM (He only, FIG. 3a). The injection of 10 SCCM $O_2$ in the capillary electrode leads to a slight reduction of the plasma jet length, while the injection of an equivalent amount to the plasma-forming gas leads to a drastic reduction of the length. Such decrease in optical emission implies a decrease in the density of excited atomic and molecular species having radiative transitions in the visible range. Since several excitation channels involve collisions with electrons and He metastables, the decrease of the optical emission can be seen as a reduction in the density of those populations. The actual situation is slightly more complex though. Preliminary investigation of the jet using optical emission spectroscopy revealed that the emission from excited atomic O increased with $O_2$ injection through the capillary electrode and collapsed with the injection of $O_2$ with the plasma-forming gas. It may be inferred from this that the electrons and He metastables are used to dissociate and excite the $O_2$ injected through the capillary electrode at the expense of $N_2$ (ambient air) dissociation/excitation. With $O_2$ injected with the He flow, a drastic overall reduction of the optical emission is observed suggesting that the plasma in the plasma-forming region is quenched.

Figure 4A:
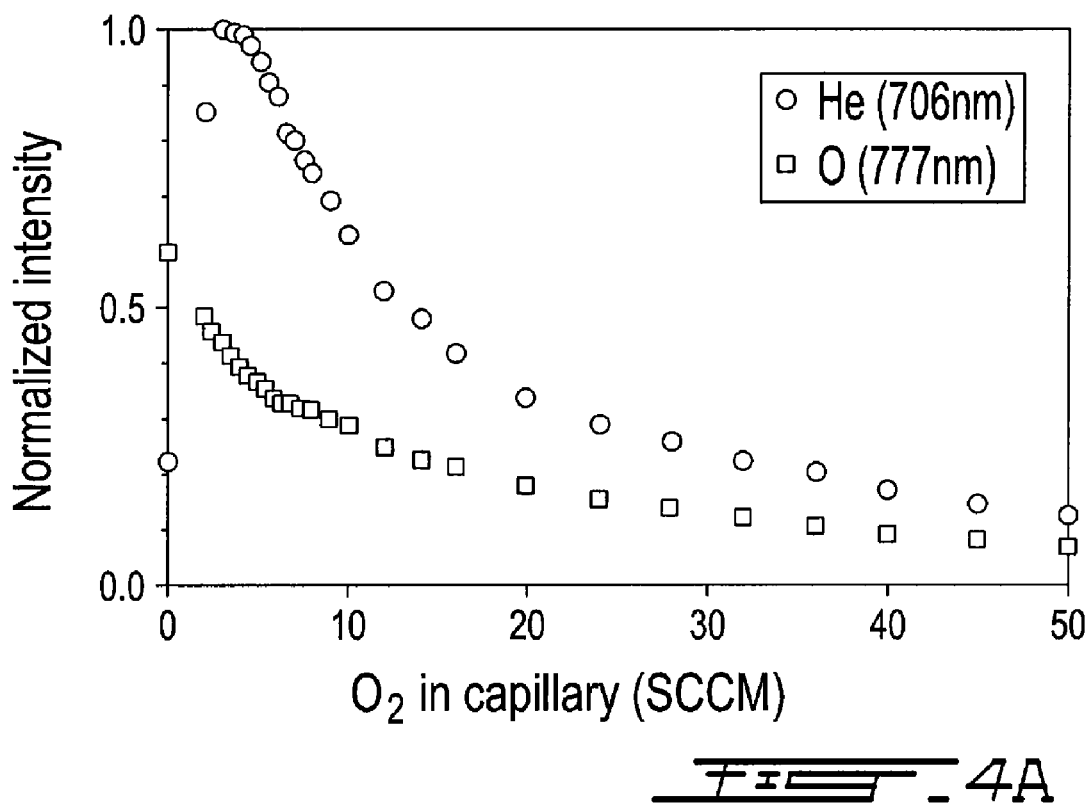
FIG. 4 show normalized peak in the atomic line emission intensity of a) O (777 nm) and He (706 nm) at the nozzle exit for different flow rates of $O_2$ in the capillary electrode; axial distribution of the normalized peak in the atomic line emission intensity of b) O (777 nm), c) He (706 nm) and d) $N_2$ (357 nm) for different He flow rates.

From the above telescopic image analysis and the preliminary spectroscopic investigation, it is found that adding $O_2$ through the capillary electrode is more efficient than adding it with the plasma-forming gas. The amount of $O_2$ added in the capillary electrode may then be optimized in order to get the maximum generation of O atoms. As a measure of the atomic O production the peak intensity of the radially integrated excited O atomic emission line at 777 nm, measured along the jet axis, is used. FIG. 4 show the relative intensity profiles of the O (777 nm) line along with some other monitor lines of He and $N_2$. All emission intensities are normalized with respect to the maximum emission intensity of the O (777 nm) line. As can be seen in FIG. 4a (1 SLM He at ≈1 W), 3 SCCM of $O_2$ injected in the capillary electrode produces an emission maximum from the O (777 nm) line. This flow rate corresponds to an $O_2$/He volumetric ratio of 0.3%. The gas temperature under those conditions is ~55° C. (Note that this gas temperature can be slightly too elevated for bio-applications—i.e. skin and cells treatments—and thus, a continuous movement of the torch over the surface of interest might be required in order to reduce the local thermal load).

Figure 4B:
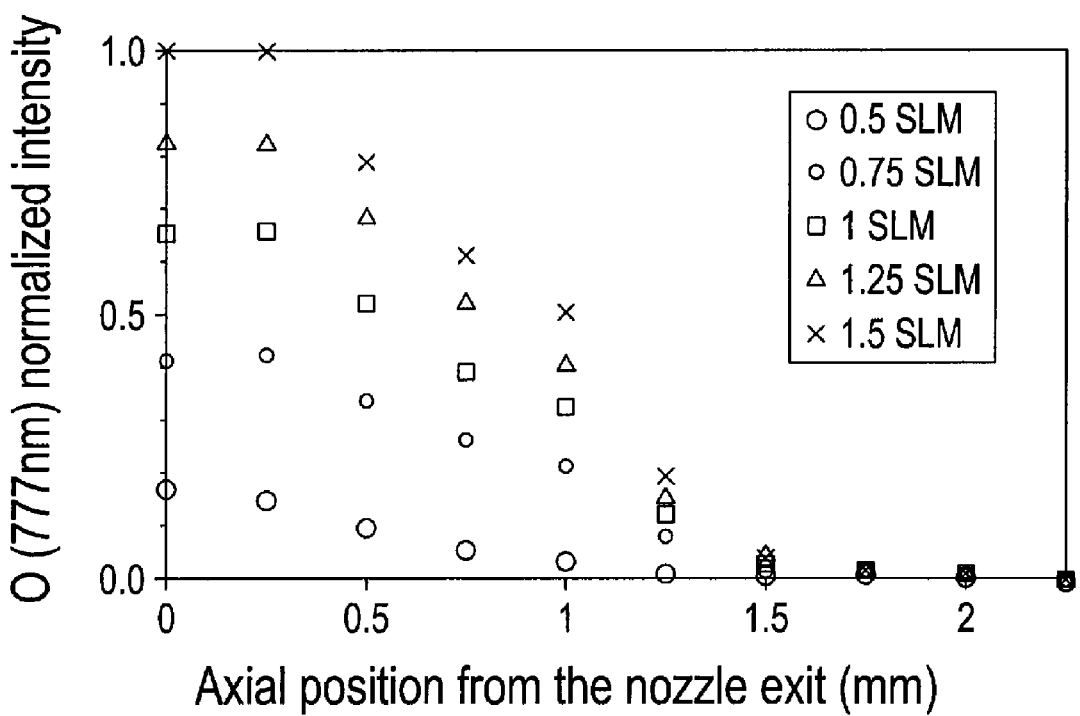
Figure 4C:
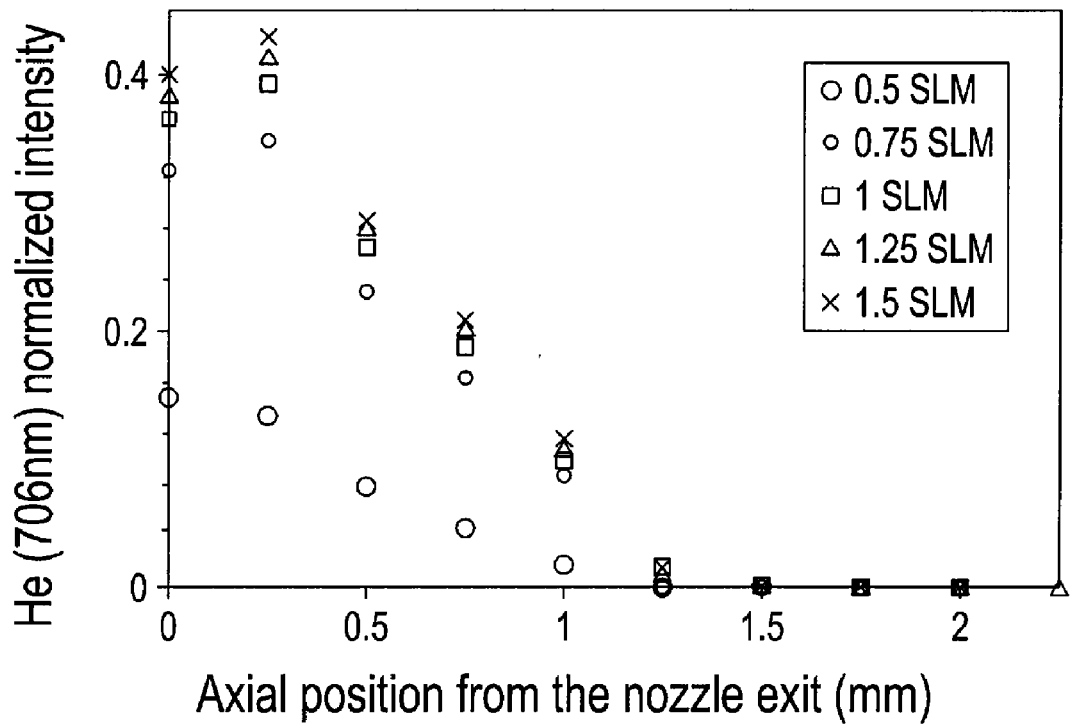
Figure 4D:
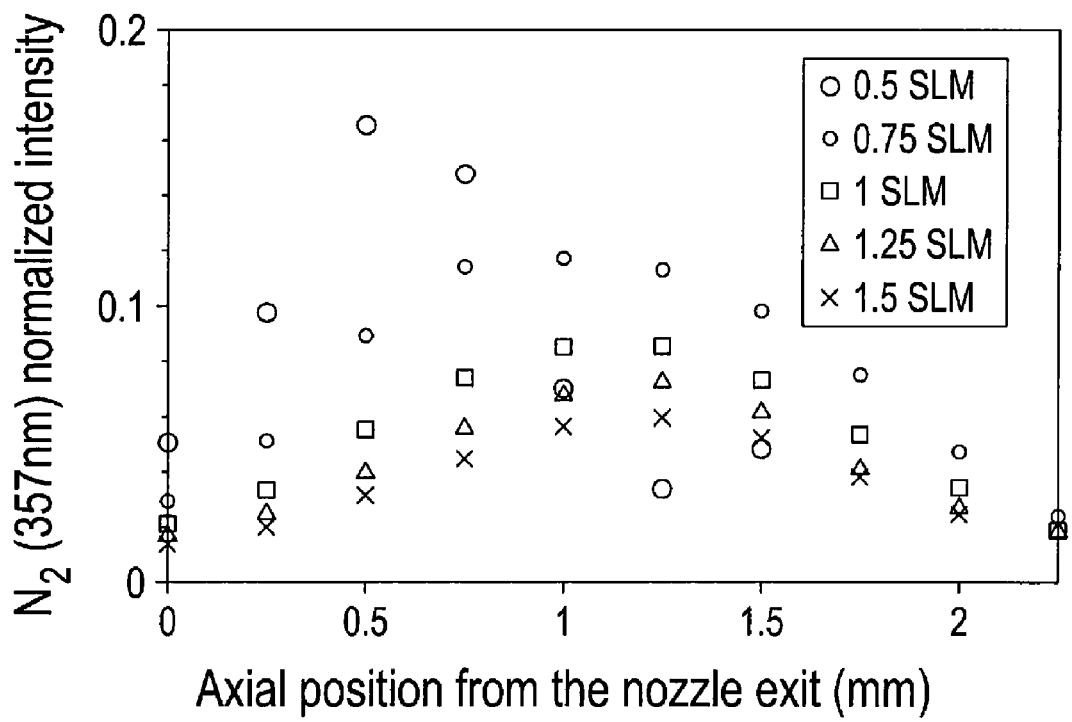

The He gas flow rate is also optimized to reach the maximum emission from the excited O atoms. During this series of experiments, the $O_2$/He volumetric flow rate ratio of 0.3% is kept constant independently of the He flow rate and torch power. As can be seen in FIG. 4b, the increase in He flow rate causes an increase of the excited O emission (777 nm line) at the nozzle exit. One can attribute this phenomenon to a more significant axial transport: the isolines for the particle densities are stretched further downstream with the increase of the plasma gas flow. At 1.5 SLM He, the production of excited O atoms is highest and the gas temperature is slightly lower than at 1.0 SLM due to the increased convective cooling (~45° C. versus ~55° C.). It is interesting to note that the intensity of the He (706 nm) line seems to saturate around 1.5 SLM while the O (777 nm) line does not. This phenomenon can be attributed to the fact that the upper energy level of the He (706 nm) transition is much larger than the O (777 nm) transition (22.72 eV versus 10.74 eV). By optimizing the production of excited He atoms, the production of metastable He atoms (upper energy levels ~20 eV) is optimized in turn. Since the metastable states have much longer lifetimes, those species are found even further downstream the plasma jet and potentially, contributing too to the formation of excited O. The increase of the He flow rate has another positive effect: the reduction of air entrainment in the plasma jet (see FIG. 4d). At a flow rate of 0.5 SLM He, the spectral emission of one of the strong emission lines of air, $N_2$ at 357 nm, is as strong as the spectral emission lines of He (706 nm) and O (777 nm) reported in FIG. 4b and FIG. 4c, respectively. However, for He flow rates of 0.75 SLM and higher, the emission from the $N_2$ line becomes much less significant than for the He and O lines.

In summary, it is shown that the present torch operating at ≈1 W in a 1.5 SLM flow of He produces a small-scale plasma jet (~3 mm long by 500 µm diameter at the nozzle exit) with a gas temperature of ~45° C., which is suitable for bio-applications. A volumetric $O_2$/He ratio of 0.3% gives rise to the maximum production of excited O atoms.

Interestingly, the present torch allows an electrical de-coupling with the surface under treatment, i.e. this surface is not part of the electrical circuit of the torch. Upon application of an RF excitation, the glow discharge is ignited and confined to the inter-electrode region, between the capillary electrode 14 and the ground electrode 24, which has the shortest path and thus, the current flow is restricted to the power supply-plasma torch system. The only exception to this situation would be when a grounded surface is being treated at working distances shorter than the gap between the two electrodes 14 and 24. Note that the electrical de-coupling does not imply that the surface is not receiving charged particles from the plasma stream: it simply implies no current through it. Thus, tissue damages associated with local electrical heating can be avoided with the proposed device.

Figure 5:
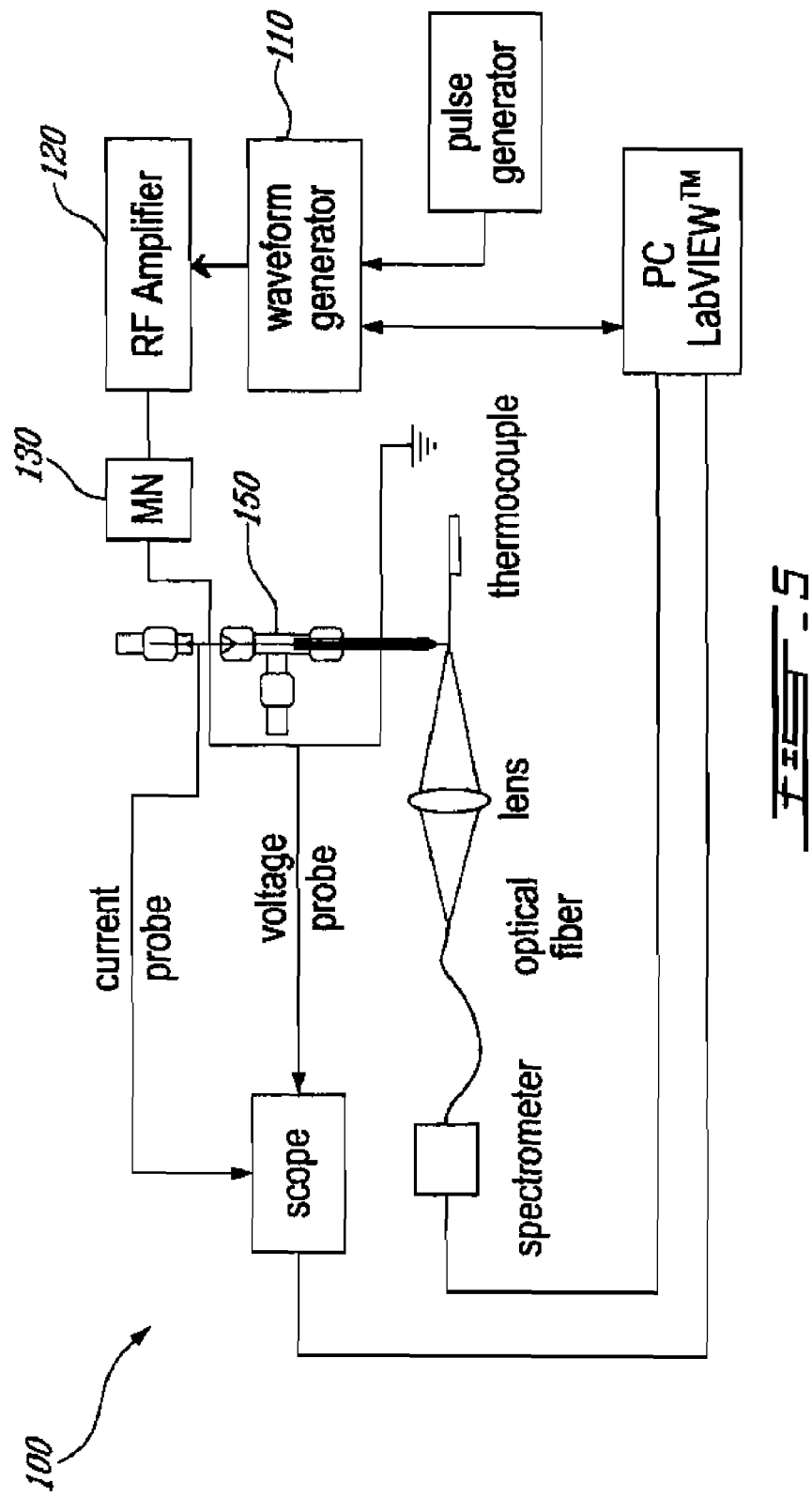
FIG. 5 is a schematic of a system using a torch according to an embodiment of the present invention.

An embodiment of a system 100 including the plasma source of the present invention is illustrated in FIG. 5. The system 100 comprises a plasma source 150, a radio frequency signal generator-amplifier-matching network system for powering the capillary electrode of said source; and a gas delivery unit, which supplies a variety of gases to the source 150. The plasma is induced using a radio frequency RF signal generated by a waveform generator 110 set at a carrier waveform frequency and amplified with a broadband RF amplifier 120). A series inductor 130, referred to as a matching network MN, is used in order to provide near-resonance circuit conditions.

The plasma source 150 may be mounted on a 3-axes support allowing the micrometric displacements necessary for precise optical measurements and surface treatments, for example.

The system 100 has a number of characteristics, including: a torch configuration with a concentric capillary electrode in order to form a well-defined plasma jet, to separate the plasma-forming and reactive species production zones, and to avoid (electrical) coupling between the plasma and substrate; use of a low-breakdown voltage gas having high-energy metastable states and enabling the excitation of reactive species in the plasma afterglow; rapid transport of the reactive species formed in the afterglow to the surface of interest; and amplitude modulation of the radio-frequency carrier signal in order to operate the device at low power levels suitable for bio-applications, yet enabling the efficient production of reactive species.

Helium allows operation at relatively low voltage under atmospheric pressure and AC excitation conditions (Yokoyama T, Kogoma M, Moriwaki T and Okazaki S 1990 *J. Phys. D: Appl. Phys.* 23 1125-1128) and is known to provide excellent excitation conditions for emission spectroscopy work (Massines F, Gouda G, Gherardi N, Duran M and Croquesel E 2001 *Plasmas and Polymers* 6 35-79). Long-lived He metastable states provide excitation conditions in the decaying plasma: it is known that under low-frequency excitation (i.e. kHz), the He metastables provide seed electrons for the re-ignition of the discharge every half-cycle. It is also believed that the long-lived high-energy He metastable states ($\approx$20 eV) can dissociate and ionize light molecules such as $O_2$. In a torch configuration with injection of the source of reactive species downstream of the plasma-forming region, the decaying He metastable atoms thus act as an excitation source. Such a configuration was used by Jin et al (Jin Q, Zhu C, Borer M W, Hieftje G M 1991 *Spectrochim. Acta B* 46 417-430) where the analytes to be excited were injected downstream of the microwave plasma-forming region. Bilgic et al (Bilgic A M, Prokisch C, Broekaert J A C, Voges E 1998 *Spectrochim. Acta B* 53 773-777) calculated the electric field at the nozzle of the microwave torch and indeed, distinguished a plasma generation region from the excitation region for the analytes.

Molecular oxygen ($O_2$), which forms strong oxidizers once injected into the He plasma, is used as the source of reactive species in the present study (up to 10 SCCM). $O_2$-containing plasmas are known to provide efficient sterilization conditions due to their etching capability and therefore, are of interest for bio-applications (see: Moreau S, Moisan M, Tabrizian M, Barbeau J, Pelletier J, Ricard A and Yahia L' H 2000 *J. Appl. Phys.* 88 1166-1174; Moisan M, Barbeau J, Moreau S, Pelletier J, Tabrizian M and Yahia L' H 2001 *Int. J. Pharm.* 226 1-21; Kelly-Wintenberg K, Montie T C, Brickman C, Roth J R, Carr A K, Sorge K, Wadsworth L and Tsai P P Y 1998 *J. Ind. Microbio.* 20 69). Atomic oxygen is produced by electron impact dissociation (e-+$O_2\rightarrow$e-+2O) and by dissociative attachment (e-+$O_2\rightarrow$O+O—) (NIST *Handbook of Atomic Spectroscopic Data* (http://physics.nist.gov/PhysRefData/Handbook)). It was suggested that the impact dissociation of $O_2$ by high energy (19.8 eV) He metastable atoms (He ($2^3$S)+$O_2\rightarrow$He+2O) is another possible mechanism for the production of O (see: Yokoyama T, Kogoma M, Moriwaki T and Okazaki S 1990 *J. Phys. D: Appl. Phys.* 23 1125-1128; Wang S, Schulz-von der Gathen V and Dobele H F 2003 *Appl. Phys. Lett.* 83 3272-3274; Bell E, Parenteau N, Guay R, Nolte C, Kemp P, Bilbo P, Ekstein B and Johnson E 1991 *Toxic. In vitro* 5 591-596).

Lastly, an important flow rate of helium is used in an attempt to minimize the ratio of the gas convection to chemical reaction (recombination) time scales. This favors the rapid transport of newly created radicals and excited species to the surface under treatment.

Under no plasma conditions, an annulus flow of 1 SLM of He between the capillary electrode and the nozzle exit gives rise to a He mean gas velocity of 172 m/s, which value corresponds to a Re number of approximately 205 (laminar flow conditions) (Bird R B, Stewart W E and Lightfoot E N 1960 *Transport phenomena* (New-York: John Wiley & Sons)). If one neglects the presence of the capillary electrode at the nozzle exit, a flow of 1 SLM of He gives rise to a mean gas velocity of 85 m/s at the nozzle exit and a corresponding Reynolds number (Re) of 351. At 10 SCCM in the capillary, $O_2$ is injected at a mean gas velocity of 7 m/s. The corresponding Re is approximately 75. Thus, laminar and subsonic flow conditions prevail at the nozzle exit under cold flow conditions. The important velocity difference between the He and $O_2$ gas flows rates causes a significant shear at the injection point thus favoring the mixing of the two gas streams.

For characterization purposes in the present study, Helium (99.998% purity) or a certified mixture of He+1 v/v % $O_2$ (±5%) is used as a plasma-forming gas. Extra dry oxygen (99.6% purity) is injected through the capillary electrode of the torch 150 as a source of reactive species. The gas flow rates are regulated using thermal mass flow controllers. The plasma jet temperature is measured using a 0.5 mm-OD, ungrounded and shielded type K thermocouple. Pictures and optical emission of the plasma jet are captured with a telemicroscopic camera and a low-resolution UV-VIS spectrometer. A bi-convex lens (50 mm-diameter, 15 cm focal length) is used to collect the plasma emission and to focus it onto a 400 μm optical fiber attached to the spectrometer. The optical response of the system is calibrated with a tungsten filament lamp over the 200-850 nm wavelength range.

Figure 6:
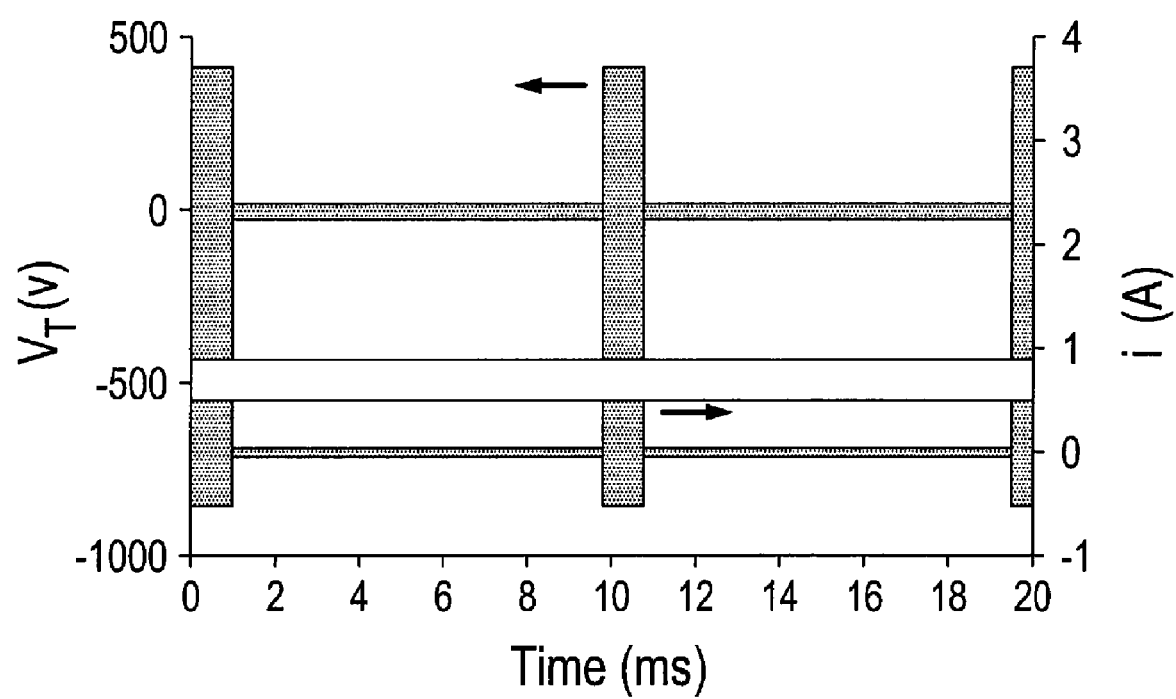
FIG. 6 is a representative example of a RF circuit current (i) and voltage pulses ($V_T$) applied to a torch according to the present invention operating with 1 SLM He and 10% duty cycle.

FIG. 6 shows typical voltage and circuit current signals of a torch of the present invention, using He (1 SLM) as the plasma-forming gas while the duty cycle and pulsation rate of the RF excitation are 10% and 100 Hz, respectively. The current signal reveals the complete extinction of the discharge following every pulse and the ease of re-ignition. The breakdown voltage in He is measured by slowly increasing the voltage applied to the torch until the onset of light emission. At the breakdown voltage, the discharge ignites around the center capillary electrode were the electric field is most intense. The discharge spreads inside the volume available as the voltage is further increased. The breakdown voltage of the torch is approximately 220 $V_{pk-to-0}$ (±2%). This low value is attributed to the geometrical amplification of the electric field at the capillary electrode surface. In fact, approximate calculations of the electric field at the breakdown voltage and of the geometrical amplification factor β at the surface of the capillary electrode (with respect to the planar geometry) give values of $\approx 5\times 10^5$ V/m and 4.4, respectively. Note that this breakdown electric field value compares well with the value of $\approx 2\times 10^5$ V/m obtained by extrapolation of the Paschen curve data reported for the high-frequency breakdown of He (Brown S C 1993 *Basic Data of Plasma Physics* (New York: AIP Press) 336 p.). As a comparison, the reported sustaining (i.e. breakdown) voltage for the plasma needle spreads from 100 $V_{pk-to-0}$ to 140 $V_{pk-to-0}$ (Stoffels E, Flikweert A J, Stoffels W W and Kroesen G M W 2002 *Plasma Sources Sci. Technol.* 11 383-388. Kieft I E, v d Laan E P and Stoffels E 2004 *New J. Phys.* 6 1-14)

FIG. 7 shows a schematic of the electrical circuit considered for an impedance matching study. According to a usual model (Baker H J 1996 *Meas. Sci. Technol.* 7 1631-1635), the plasma torch is represented by a capacitor $C_T$ [F] mounted in series with a resistor $R_T$ [Ω]. The complex impedance of the torch is thus described as (s=Laplace domain variable):

$$Z_T(s = j\omega) = \frac{\tau_T s + 1}{C_T s} = R_T - \frac{j}{\omega C_T} \qquad (1)$$

where $\tau_T = R_T C_T$ [s] is the torch's time constant and $\omega = 2\pi f$ [rad/s] is the carrier frequency in angular units. The complex impedance of the voltage probe is:

$$Z_p(s = j\omega) = \frac{R_p}{\tau_p s + 1} = \frac{R_p}{1 + \omega^2 \tau_p^2} - \frac{R_p \omega \tau_p}{1 + \omega^2 \tau_p^2} j \qquad (2)$$

where $\tau_p = R_p C_p$ is the probe's time constant. At f=13.56 MHz, the complex impedance of the voltage probe ($R_p$=10 MΩ, $C_p$=8 pF) is $Z_p$=0.215-1467 j □. This small impedance value implies that the presence of the probe is likely to affect the dynamics of the electrical circuit and thus, must be accounted for in the analysis. The complex impedance of the torch-voltage probe system is given by:

$$Z_{T+p}(s = j\omega) = R_p \frac{(\tau_T s + 1)}{\tau_p \tau_T s^2 + \tau' s + 1} \qquad (3)$$

$$= \frac{R_p}{(1 - \omega^2 \tau_p \tau_T)^2 + \omega^2 \tau'^2}[(1 - \omega^2 \tau_p \tau_T + \omega^2 \tau_T \tau') - \omega(\tau' - \tau_T + \omega^2 \tau_p \tau_T^2)j]$$

with $\tau' = \tau_T + \tau_p + R_p C_T$. The phase shift, $\phi[°]$, between the torch voltage, $V_T (= Z_{T+p} \cdot i)$ and circuit current, i, is given by:

$$\phi(\omega) = \frac{360}{2\pi} \cdot \tan^{-1}\left(-\frac{\omega(\tau' - \tau_T + \omega^2 \tau_p \tau_T^2)}{1 - \omega^2 \tau_p \tau_T + \omega^2 \tau_T \tau'}\right) \qquad (4)$$

From the measurement of $|Z_{T+p}|=V_{T\text{-}RMS}/i_{RMS}$ and $\phi$ during the "ON" phase the torch's resistance ($R_T$) and capacitance ($C_T$) values may be determined directly using equations (3) and (4). A matching network may be mounted in series between the amplifier and the torch in order to achieve near-resonance conditions. The "cold" capacitance of the torch assembly (i.e. when the glow discharge is not yet ignited) is used in order to determine a suitable value for L. This capacitance is estimated by representing the torch assembly as a set of two concentric metal conductors of length l separated by a dielectric gap, as follows:

$$C_T^{Cold} = \frac{2\pi l \varepsilon_0}{\left(\frac{\ln(r_2/r_1)}{\varepsilon_{pr}} + \frac{\ln(r_3/r_2)}{\varepsilon_{qr}}\right)} \approx 1.5 \text{ pF} \qquad (5)$$

In the above relation, l=5 cm, $\varepsilon_{pr}$=1 is the relative dielectric constant of air (or He), $\varepsilon_{qr}$=3.75 is the relative dielectric constant of quartz, $r_1$=0.1778 is the outside radius of the capillary electrode, while $r_2$=1 mm and $r_3$=2 mm are the inside and outside radii of the quartz tube, respectively. The circuit resonance is observed when:

$$L_o = \frac{R_p \tau}{1 + \omega^2 \tau^2} \qquad (6)$$

with $\tau = R_p(C_T^{Cold} + C_p)$. At f=13.56 MHz, one finds $L_o$=14.5 μH. On the other hand, the actual circuit is slightly de-tuned to accommodate the larger capacitance values expected when the glow discharge is present, and to account for the additional capacitive and inductive sources, which were not considered in the analysis (ex. ground leads). It is found that an inductance value of 6.3 μH (measured with a simple RL circuit (f=100 kHz and R=3.3Ω) leads to easy ignition of the glow discharge and electrical stability of the plasma in the desired torch power range. The inductor is built from a coated copper wire wound onto a PVC tube using the following design relation (DeMaw D 1979 *The radio Amateur's Handbook* (Newington: American Radio relay league) p. N/A):

$$L = \frac{d^2 n^2}{45.7d + 102w} \qquad (7)$$

In the above relation, d [cm] is the outside diameter of the PVC tube, n is the number of turns, and w [cm] is the length of coil wound on the tube. Equation (7) indicates that an n=8.5 turns inductor built with w=1.3 cm on a d=6 cm tube has a theoretical inductance value of 6.4 μH, which is close the measured value of 6.3 μH.

FIG. 8 shows one complete cycle of the 13.56 MHz excitation voltage applied to the torch and circuit current measured for conditions representative for all situations investigated in this study (with duty cycle DC=10%). The peak torch voltage and current are 405 $V_{pk\text{-}to\text{-}0}$ and 0.46 $A_{pk\text{-}to\text{-}0}$ respectively, while the phase shift between both signals is −83° (±1.5%). The corresponding modulus of the impedance and power delivered to the torch-voltage probe system are $|Z_{T+p}|$=880Ω and $P_{T+p}=V_{T\text{-}RMS} \cdot i_{RMS} \cdot \cos\phi \cdot DC$=1.14 W, respectively. Note the absence of current spikes associated with the formation of filamentary discharge. Note also that the circuit current leads the torch voltage by a phase angle of −83°, revealing the highly capacitive nature of the torch-voltage probe system. An abacus constructed using equations (3)-(4), with $R_T$ and $C_T$ as independent parameters, is used to determine the plasma torch electrical parameters ($R_T$ and $C_T$) from the impedance $Z_T$, and phase angle $\phi$ measurements.

Figure 9:
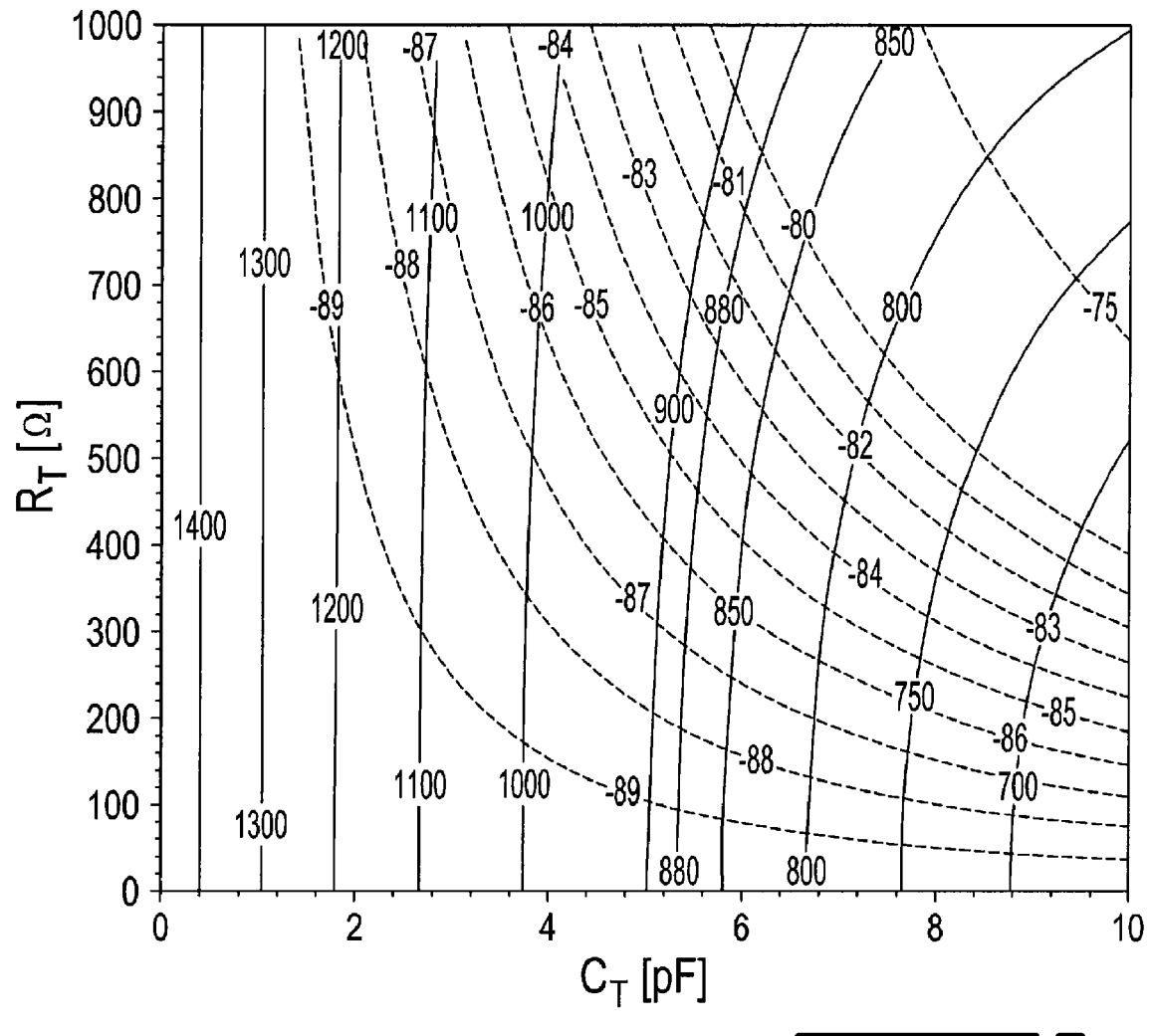
FIG. 9 is a contour plot of the modulus of the torch/voltage probe system's complex impedance, ($|Z_{T+p}|$), and phase shift (θ) versus the torch resistance ($R_T$) and capacitance ($C_T$)

The continuous lines plotted on FIG. 9 correspond to constant values of $|Z_{T+p}|$ while the dashed lines are associated with constant values of □ in the $R_T$-$C_T$ plane. For $|Z_{T+p}|$=880Ω and $\phi$=83°, we find $R_T \approx 640\Omega$ and $C_T \approx 5.8$ pF and consequently, the complex impedance of the torch is $Z_T \approx 640$-

2024 j Ω (at f=13.56 MHz). The resistive power dissipated in the torch is calculated using relation (8) below:

$$P_T = \frac{V_{R_T-RMS}^2}{R_T} \cdot DC = \frac{\left(V_{T-RMS} \cdot \frac{R_T}{|Z_T|}\right)^2}{R_T} \cdot DC \quad (8)$$

At 10% duty cycle, the resistive power dissipated in the torch is 1.14 W. Consequently, all the power supplied to the torch/voltage probe system is dissipated in the torch (since $R_T << R_p$). The power density under those conditions is 15 W/cm$^3$ (the volume occupied by the glow discharge is ≈76 mm$^3$). Assuming that all the resistive power is used to heat up a substrate exposed to the plasma jet, one obtains a heat flux at the nozzle exit of 6×10$^6$ W/m$^2$. In reality, this flux is expected to be significantly lower due to the radiative losses of the torch, and the spreading of the plasma jet over working distances of 1 to 2 mm.

Figure 10:
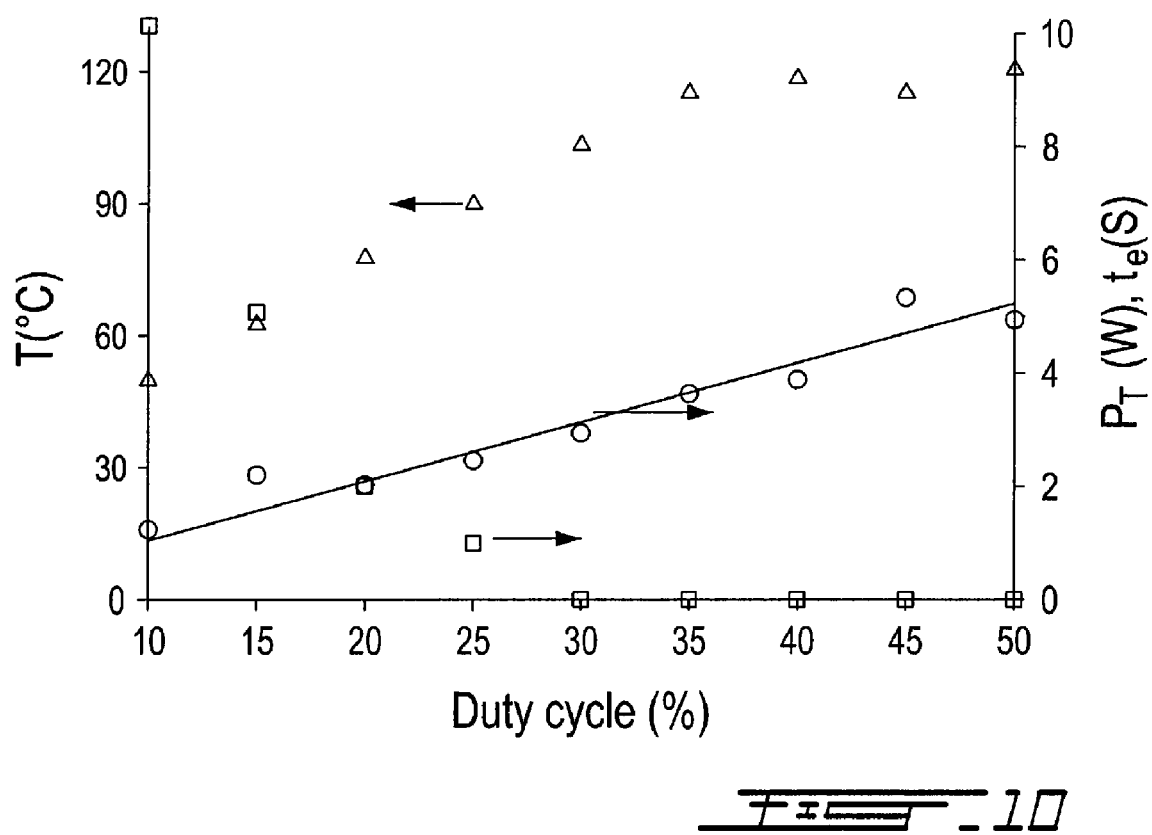
FIG. 10 presents the measured resistive power $P_T$ [W] (o) delivered to the torch; the gas temperature T[° C.] (Δ) measured downstream of the nozzle exit as a function of the pulse duty cycle (DC); and the exposure time to skin $t_e$ [s] ( ), versus the RF pulse duty cycle for 1 SLM He.

FIG. 10 presents the measured resistive power delivered to the torch, $P_T \approx P_{T+p}$, and the gas temperature measured by the thermocouple 1.5 mm downstream of the nozzle exit, as a function of the pulse duty cycle (DC). The results show that the torch power can be continuously modulated over the 1-5 W range by varying the duty cycle from 10 to 50%. Since both the torch voltage and circuit current during the "ON" phase should not be affected by the duty cycle, one expects a linear increase of the resistive power with the duty cycle; this is indeed observed in FIG. 7 (trend line slope of 0.1 W/% (R$^2$=0.93)).

Also plotted in FIG. 10 is an approximate measurement of the maximum plasma exposure time to the skin ($t_e$). This time lapse is obtained by exposing a finger to the plasma jet, approximately at the same location as the thermocouple, until a burning sensation is felt. At 10% duty cycle, the gas temperature is 50 (±2) ° C., while this number increases to 122 (±2) ° C. at 50%. It is found that a gas temperature of 50° C. is tolerable over a 10 second treatment time. As a comparison, the thermal neutrality zone for human skin spreads from 26 to 36° C. (Malenfant A, Forget R, Amsel R, Papillon J, Frigon J-Y and Choiniére M. 1998 *Pain* 77 241-251), and exposure to a heat source held at a temperature above 50° C. causes a burning sensation (Ziegler D, Mayer P, Wiefels K and Gries F A 1988 *Pain* 34 1-10; Adams R D and Victor M 1993 *Principles of neurology* (New York: McGraw Hill Inc.) 1394 p.). The temperature of the substrate area exposed to the plasma stream may be easily reduced by decreasing the power dissipated in the plasma or by reducing the exposure time.

As discussed hereinabove, the downstream injection of the source of reactive species allows de-coupling the plasma-forming region from the excitation region. The addition of 10 SCCM O$_2$ through the capillary electrode does not disturb the torch voltage and circuit current characteristics. However, the addition of the same amount of O$_2$ to the He plasma-forming gas leads to a 3% increase of the torch voltage and a 4% decrease of the circuit current (results not shown here). No appreciable effect to the shape of the electrical waveforms is observed. It is suspected that the addition of a trace amount of an electronegative gas to the inert plasma-forming gas causes a reduction of the electron density and consequently, a reduction of the electrical conductivity. More dramatic changes are observed with the visual appearance of the plasma jet, as seen in FIG. 3. The outer left and right figures reveal a whitish plasma cone, its color characteristic of He plasmas, followed by a bluish afterglow. It is interesting to notice a flow structure near the nozzle exit, suggesting a transition to supersonic conditions (FIGS. 2a-2b). One can speculate that the additional acceleration of the flow is due to gas expansion caused by heating, and to some MHD pumping. The injection of O$_2$ through the capillary electrode led to a slight elongation of the plasma cone, without significantly affecting the overall length of the jet. On the other hand, when a similar amount of O$_2$ was added to the plasma-forming gas, the jet length reduced to less than 1 mm. The plasma jet disappeared completely at a slightly higher O$_2$ flow rate.

Those observations are confirmed with the optical emission spectra taken 1 mm downstream of the nozzle exit (FIG. 11). All emission spectra reveal the presence of excited He and atomic oxygen in the plasma jet, as well as some excited air molecules (entrained in the plasma jet). The addition of O$_2$ to the plasma-forming gas leads to a significant decrease of the He emission (up to 90% for the 2$^3$P-3$^3$S transition of He at 706 nm) and air molecules emission, but without affecting the atomic oxygen emission (3$^5$S-3$^5$P at 777 nm). This suggests that a significant fraction of the plasma electrons are used to produce O-containing species from the O$_2$ molecules present in the plasma-forming gas (i.e. excited O$_2$ and O, and O—), leaving fewer electrons to collide and excite the He atoms and entrained air molecules.

The poor spectral resolution of the spectrometer does not permit differentiation of the spectral emission of N$_2$ (309, 316 and 391 nm) and N$_2^+$ (427 nm) from the Schumann-Runge O$_2$ system, OH band heads (Gaydon A G 1957 *The Spectroscopy of Flames* (New York: John Wiley & Sons, Inc.) pp. 243-244), and O$_2^+$ emission at 427 nm. The probable formation paths of O$_2^+$ in a He plasma are direct electron-impact ionization (e-+O$_2$→2e-+O$_2^+$) and Penning ionization (He(2$^1$S)+He (2$^3$S)+O$_2$→He+O$_2^+$+e-(Lee Y-H, Yi C-H, Chung M-J, Yeom G Y 2001 *Surf. Coat Technol.* 146-147 474-479; Seo D C and Chung T-H 2001 *J. Phys. D: Appl. Phys.* 34 2854-2861). Since N$_2$ represents 79% of air, its emission is likely to be significant with respect to O$_2$ and OH emission. The presence of N$_2$ lines (337, 357, 375, 380 and 405 nm) and N$_{2+}$ lines (353, 391, 427 and 470 nm) in FIGS. 11a-b clearly reveals air entrainment. Such N$_2$ and N$_2^+$ lines were reported elsewhere (Guerra-Mutis M H, Pelaez U C V and Cabanzo H R 2003 *Plasma Sources Sci. Technol.* 12 165-169; Massines F, Gouda G, Gherardi N, Duran M and Croquesel E 2001 *Plasmas and Polymers* 6 35-79; Tanabe K, Haraguchi H and Fuwa K 1983 *Spectrochim. Acta B* 38 49-60)

Figure 12A:
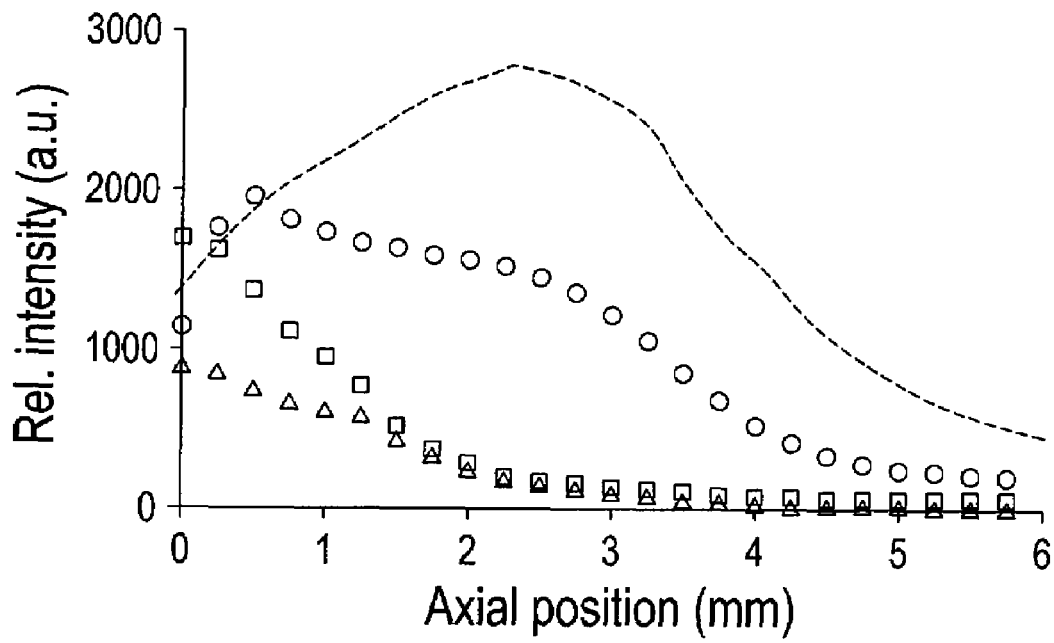
FIG. 12 show axial profiles of the peak intensity of selected atomic emission lines for $P_T$≈1 W: a) 1 SLM He with 10 SCCM $O_2$ in the capillary electrode: $N_2$ (--) at 337 nm, $N_2^+$(o) at 391 nm, He (□) at 587 nm and $H_\alpha$ (Δ) at 656 nm; b) O emission at 777 nm for 1 SLM He (–), 1 SLM He with 10 SCCM $O_2$ in the capillary electrode (■), and 1 SLM He+1 v/v % $O_2$ as plasma-forming gas (▲)

Massines and Gouda (Massines F, Gouda G, Gherardi N, Duran M and Croquesel E 2001 *Plasmas and Polymers* 6 35-79) mentioned that N$_2$ molecules are very effective at quenching the He metastables resulting in the excitation of N$_2$, and subsequent spectral emission. For instance, the N$_2^+$ emission at 391 nm is attributed to Penning ionization of N$_2$ with He metastables (Nersisyan G and Graham W G 2004 *Plasma Sources Sci. Technol.* 13 582-587). Thus, the emission lines at 391 nm and 337 nm, present up to 6 mm downstream of the nozzle exit, seen in FIG. 12a, indicate the presence of He metastables in the plasma afterglow.

Atomic oxygen emission resulting from the 3$^5$S-3$^5$P transition at 777 nm is observed on all spectra, including the spectrum of FIG. 11a, where no oxygen is voluntarily added, thus confirming the entrainment of ambient air in the plasma jet.

Figure 12B:
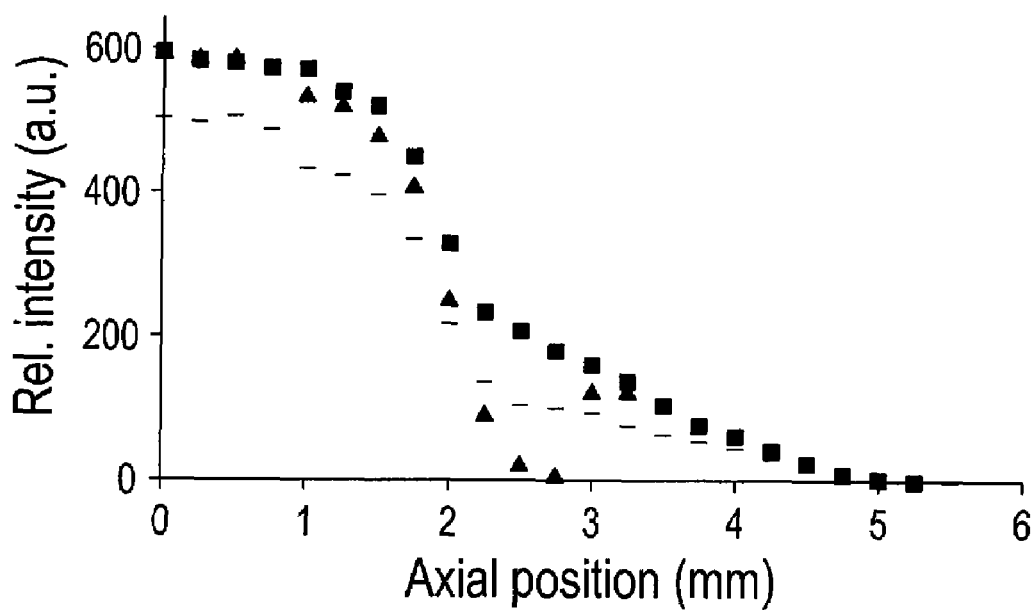

In FIG. 12b, each atomic oxygen emission profile shows a maximum at the nozzle exit, and a monotonic decrease with the distance from the nozzle. In the case of O$_2$ injection in the capillary electrode, the O profile stretches further downstream of the nozzle exit. This is attributed to the higher density of O$_2$ introduced in the excitation region, and the slightly higher jet momentum (due to the O$_2$ flow). The monotonic decrease of the excited O emission, and the peak in the excited $N_2$ species emission intensities, located downstream of the nozzle exit, are indicators of the decay of the electron and metastable He atom densities. Finally, it is suspected that the density of ground state oxygen atoms is significant in the plasma afterglow since the 777 nm transition originates from a high energy level (9.146 eV).

Other He neutral lines can be identified in FIG. 11 ($3^1P$-$2^1S$ at 501 nm; $2^3P$-$3^3D$ at 587 nm; $2^1P$-$3^1D$ at 667 nm and $2^1P$-$3^1S$ at 728 nm). The strong emission line observed at 656 nm corresponds to the $H_\alpha$ line since water vapor molecules from the ambient air can be entrained and dissociated in the plasma jet (Herzberg G 1945 *Atomic Spectra and Atomic Structure* (New York: Dover publications) p. 24). In fact, emission from the OH molecule at 309 nm was only observed when the 656 nm line was present. OH radicals can be formed by the reaction of excited O with water vapor ($H_2O$+ O→2OH) and by electronic impact dissociation ($H_2O$+e- →H+OH+e-).

Figure 13:
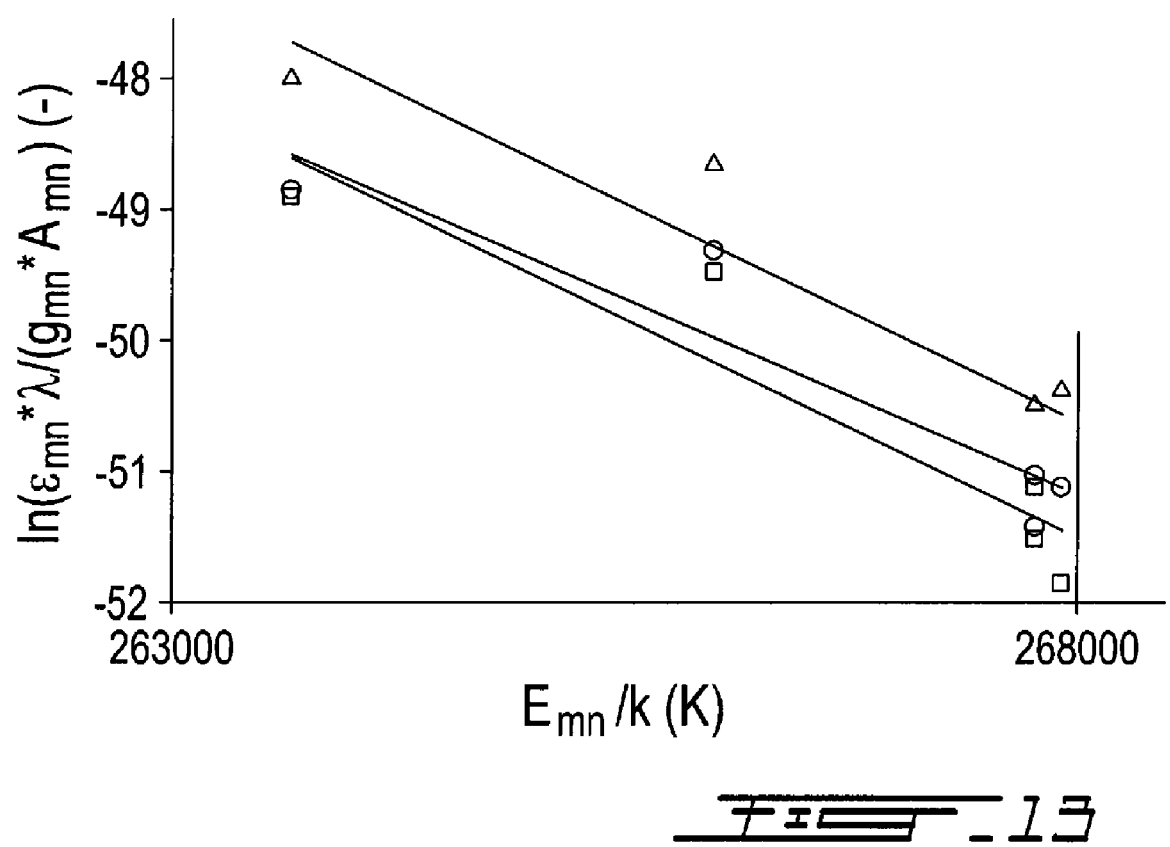
FIG. 13 shows a Boltzmann plot obtained for $P_T$≈1 W 1 SLM He and three different distances from the nozzle exit: −0.25 mm (□), 0 mm (Δ) and 0.25 mm (o). The average excitation temperature is 1573 K ($R^2$=0.88).

The line-of-sight excitation temperature of the He atoms, $T^{exc}(He)$, may be determined by the Boltzmann plot method to get a feel for the excitation conditions prevailing in the plasma afterglow near the nozzle exit plane. It is assumed that the peak intensity of each line is proportional to its total integrated intensity (Vacquié S 2000 *L'arc électrique* (Paris: CNRS Éditions) pp. 237-253), and that each line is optically thin. The neutral He atomic emission lines used to build the Boltzmann plot are the 501 nm, 587 nm, 667 nm, 706 nm and 728 nm. FIG. 13 shows the Boltzmann plot obtained with 1 SLM He at $P_T$≈1 W, where $T^{exc}(He)$ is 1573 K. For all conditions investigated, $T^{exc}(He)$ is of the order of 2000K or less. The $T^{exc}(He)$ shows a strong dependency on torch power and increases slightly with the injection of $O_2$ both in the capillary electrode and with the plasma forming gas, as seen in Table 1 below.

TABLE 1

|  | Exp # | | | | |
| --- | --- | --- | --- | --- | --- |
|  | 2 | 3 | 4 | 5 | 6 |
| Plasma gas composition | He | He + 1% v/v$O_2$ | He + 1% v/v$O_2$ | He + 10 SCCM $O_2$ capillary | He + 10 SCCM $O_2$ capillary |
| $P_T$ (W) | ≈1 | ≈1 | ≈1.25 | ≈0.6 | ≈1 |
| $T_{exc}$ (K) | 1573 | 1658 | 1739 | 1653 | 1914 |

The presence in the plasma of $O_2$, a source of electronegative species, causes an increase of the sustaining voltage and consequently, of the electric field strength. Therefore, the mean electron kinetic energy is increased, and this leads to an increase of the excitation temperature. Low excitation temperatures were also reported with other low-power atmospheric pressure plasma sources. A $T^{exc}(He)$ of ≈1900 K is reported for a capacitively-coupled plasma discharge operating at 5 W with 475 SCCM He (Yoshiki H and Horiike Y 2001 *J. Appl. Phys.* 40 L360-L362), ≈2900 K with a single needle RF discharge operating with 1 SLM He at 8 W (Kikuchi T, Hasegawa Y and Shirai H 2004 *J. Phys. D: Appl. Phys.* 37 1537-1543) and ≈3000 K for the plasma needle operating at a few hundred mW (Stoffels E, Flikweert A J, Stoffels W W and Kroesen G M W 2002 *Plasma Sources Sci. Technol.* 11 383-388).

From the above, it should now be apparent that the present invention allows producing a non-thermal plasma jet of at most 500 μm-diameter and ≈2.5 mm long at power levels ranging from 1 to 5 W. The use of pulsed RF excitations at low duty cycle (for example at 10%) allows the operation of the torch at a ≈1 W power level. Under these conditions, the gas temperature is ≈50° C., while the He excitation temperature is less than 2000 K. The addition of 1 v/v % $O_2$ to the plasma-forming gas leads to a drastic contraction of the jet. Alternatively, the injection of 10 SCCM $O_2$ through the capillary electrode leads to the production and transport of atomic O further downstream in the plasma jet, without significantly affecting the electrical properties of the plasma source and jet length.

The capability to produce and transport reactive species under non-thermal plasma conditions is of potential interest for bio-applications where precise chemical treatments of heat-sensitive materials are involved.

Therefore, the present low-power atmospheric pressure plasma torch with downstream injection of the source of reactive species allows for the formation of a narrow diameter plasma jet and the electrical decoupling of the device (the plasma torch) from the substrate under treatment. (i.e. no current transfer to the substrate).

The present torch is provided with a narrow converging nozzle which permits the acceleration of the plasma stream and the formation of a stable and narrow jet (<500 μm diameter), which allows a precise, local treatment capability; a rapid transport of excited species and radicals to the surface under treatment; a reduction of the breakdown and sustaining voltage; and an elongation of the plasma jet.

The present torch may use He or Ar or $N_2$, which species participate in the formation of reactive species in the excitation region, and enabling the excitation of reactive species in the plasma afterglow.

As the present torch with a concentric capillary electrode i) forms a well-defined plasma jet, separates the plasma-forming and reactive species production-zones, and avoids (electrical) coupling between the plasma and substrate; ii) maintains a stable plasma at low voltage, in a gas that contains high-energy metastable species, which allows for the generation of reactive species in the afterglow; iii) allows a rapid transport of the reactive species formed in the afterglow to the surface of interest; and iv) operates at atmospheric pressure, low power levels (<5 W) and voltage levels (<600 V), it may be suitable for biomedical applications for example.

It is versatile since it is capable of producing reactive species from a variety of gas mixtures without pertubation of the plasma properties. It may easily be mounted on a small robotic arm or even hand-held. The present torch and system may found applications for example in skin treatment, etching of skin cancer cells, detachment of cells, removal of skin pigmentation and deposition of temporary organic films.

People in the art should now be in a position to appreciate that the present torch is characterized by an enhanced local surface treatment capability (<500 μm diameter), low penetration depth, in-situ generation and application of active chemical species, an absence of current transfer to a surface under treatment, and absence of damaging heating.

As mentioned hereinabove, the present plasma source may be used for bio-applications such as etching of tissues and cancer cells, the detachment of cells, the removal of skin pigmentation, and the deposition of temporary organic films for example. All the above-mentioned treatments are superficial in nature due to the expected low-penetration depth of the plasma. The plasma stream produced by the new plasma source is small (500 μm-diameter or less) for precise, local treatments. Furthermore, the new source is capable of producing reactive species from a variety of gas mixtures in order to accommodate the requirements of each process.

A number of applications may be contemplated, including for example tissue surface treatment, cell modification, treatment of veins and dental cavities, use in catheters, fine surgical techniques: removal of unwanted cells/tissues, cure of skin ailments, restoration of bones/tooth enamel, cleaning of dental cavities.

The present invention therefore provides a non-invasive method of manipulating live cells using an atmospheric pressure plasma source. The atmospheric plasma can permeabilize cells, which then are able to reseal and remain viable. This method can be used both in the laboratory, to allow the introduction of specific macro-molecules into live cells for monitoring and modification, and in a clinic as a means to transfer macro-molecules to monitor or modify cellular processes, for localized cell manipulation without thermal or chemical damage.

In contrast to existing techniques, the atmospheric pressure plasma can treat a large (when mounted on a robot arm for example), or small surface area of adhered cells at one time, and yields viable cells after permeabilization.

The miniature plasma source described hereinabove was used to treat mammalian cells and to functionalize surfaces for cell culture. It was demonstrated that the plasma jet produced by the torch is able to detach cultured cells with good precision. The width of the void in the cells was approximately 1.5 times larger than the width of the nozzle exit. The cells were able to reattach and proliferate after being transferred to a new culture vessel. HepG2 cells were removed in sheets, indicating that the cell-cell adhesion was not disrupted. It is likely that either the cell-substrate adhesion proteins, or the substrate itself, were oxidized, releasing the cells. The cells were permeabilized during the treatment, as demonstrated by the diffusion of a fluorescent dye (PI) into the cell, while a proliferation test indicated that all cells were still viable. There is thus the potential for this plasma source to be used for the local removal of cells, either for isolation and analysis or ablation treatment. The plasma torch is also able to functionalize a bacterial grade PS dish promoting cell attachment and growth. Following the plasma treatment, the contact angle of the PS surface decreased from 93° to 35°. Confluent cell tracks were formed, with the width of the track corresponding to approximately twice the I.D. of the torch nozzle. It was also found that the sweep speed of the plasma torch over the surface had the biggest influence on the width of the cell track. The miniature plasma torch could be useful in biological micropatterning, and could be paired with a pre-treatment step to tailor the base layer to the needs of the application. Unlike the photolithographic techniques presently used, the present plasma-based process does not involve chemicals, which can have adverse reactions with biodegradable polymers, and is also able to pattern on 3D surfaces without the use of a mask.

Therefore, the present invention provides a plasma source able to permeabilize cells, which are then able to reseal and remain viable after few hours. Proof of concept was shown using propidium iodide, a fluorescent biological stain (668 kD marker) that was able to diffuses into the treated cells. The cells have been shown to remain viable and to reseal within 24 hrs. When staining four hours after plasma treatment, all cells were observed to fluoresce, whereas staining 24 hours after plasma treatment resulted in most cells remaining non-fluorescent, indicating that they were able to repair their membrane.

The short-term application of this invention is for use in general biological laboratories. Live cell permeabilization is used to allow the passage of compounds like dyes, DNA, proteins and markers into cells to analyze or alter cell function. The plasma source could be contained in a benchtop or handheld device. Cells could easily be exposed to the plasma and the desired compound introduced to the cell. Cells would remain viable for further analysis and expansion. The potential size of the market includes all cell culture laboratories.

In the long term, the plasma source could be used as a medical device to introduce drug treatment directly into cells/tissue in a localized and precise manner.

The plasma source provides many advantages over the present technologies. When mounted on a robot arm for example, the present plasma source can easily treat a large surface area of adhered cells at one time, and yields viable cells after permeabilization.

Although the present invention has been described hereinabove by way of specific embodiments thereof, it can be modified, without departing from the spirit and nature of the subject invention as defined in the appended claims.

What is claimed is:

1. A low-power atmospheric pressure plasma source, comprising:
a ground electrode, provided on an external surface of a dielectric plasma confinement tube; and
a capillary electrode centered inside said ground electrode;
wherein a space, along the length of said confinement tube, between said capillary electrode and said ground electrode, defines a plasma-forming and plasma-confinement region, a plasma-forming gas being injected in said plasma-forming region; said capillary electrode being able to receive a source of reactive species for injection downstream of the plasma-forming and plasma-confinement region independently of the plasma-forming gas injected in said plasma-forming and plasma-confinement region and said source of reactive species is capable of producing reactive species from a variety of gas, said plasma source producing a plasma jet through a converging plasma exit.

2. The low-power atmospheric pressure plasma source of claim 1, a converging nozzle of said plasma confinement tube forming said converging plasma exit.

3. The low-power atmospheric pressure plasma source of claim 1, further comprising a source of reactive species.

4. The low-power atmospheric pressure plasma source of claim 3, the source of reactive species being conveyed through one of: i) said capillary electrode, ii) air entrained in the plasma, and iii) the plasma-forming gas.

5. The low-power atmospheric pressure plasma source of claim 1, the plasma-forming gas being one of He, Ar and $N_2$.

6. The low-power atmospheric pressure plasma source of claim 1, wherein the plasma is induced using a radio-frequency excitation.

7. The low-power atmospheric pressure plasma source of claim 6, the radio-frequency excitation being generated by an amplitude-modulated waveform generator.

8. The low-power atmospheric pressure plasma source of claim 1, operating at a power less than 5 W and voltage levels less than 600 $V_{pk-to-0}$.

9. The low-power atmospheric pressure plasma source of claim 1, the plasma-forming gas being He at a few SLM, the plasma jet produced having a diameter of less than 500 μm and a length of about 2.5 mm a breakdown voltage being about 220 $V_{pk-to-0}$.

10. The low-power atmospheric pressure plasma source of claim 1, a temperature of said plasma jet being compatible with bio-applications.

11. The low-power atmospheric pressure plasma source of claim 10, the temperature of said plasma jet being less that 50° C. for a power level of about 1 W.

12. The low-power atmospheric pressure plasma source of claim 2, further comprising a first injection line for injecting the plasma-forming gas in the space between said capillary electrode and said plasma confinement tube; and a second injection line for injecting the source of reactive gas in one of said capillary electrode and said space.

13. The low-power atmospheric pressure plasma source of claim 1, said source being one of: i) handheld and ii) mounted on a robotic arm.

14. A plasma-assisted treatment system, comprising:
 a low-power atmospheric pressure plasma source according to claim 2;
 a radio frequency signal generator-amplifier-matching network system for powering the capillary electrode of said low-power atmospheric pressure plasma source; and
 a gas delivery unit, which supplies gases to said low-power atmospheric pressure plasma source.

15. The low-power atmospheric pressure plasma source of claim 1, used for at least one of: i) cell detachment, ii) surface functionalization and iii) cell permeabilization.

16. A method for cell modification using the low-power atmospheric pressure plasma source of claim 1.

\* \* \* \* \*